(12) United States Patent
Jain

(10) Patent No.: US 10,328,129 B2
(45) Date of Patent: Jun. 25, 2019

(54) COMPOSITION AND METHOD FOR TREATING NUCLEIC ACID-RELATED EYE DISEASE

(71) Applicant: THE BOARD OF TRUSTEES OF THE UNIVERSITY OF ILLINOIS, Urbana, IL (US)

(72) Inventor: Sandeep Jain, Oak Park, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/397,595

(22) Filed: Jan. 3, 2017

(65) Prior Publication Data

US 2017/0106057 A1 Apr. 20, 2017

Related U.S. Application Data

(62) Division of application No. 14/362,589, filed as application No. PCT/US2012/051562 on Aug. 20, 2012, now Pat. No. 9,867,871.

(60) Provisional application No. 61/600,037, filed on Feb. 17, 2012, provisional application No. 61/569,604, filed on Dec. 12, 2011.

(51) Int. Cl.
| | |
|---|---|
| *A61K 38/46* | (2006.01) |
| *A61K 45/06* | (2006.01) |
| *C12Q 1/68* | (2018.01) |
| *A61K 9/00* | (2006.01) |
| *A61K 31/465* | (2006.01) |
| *A61K 45/00* | (2006.01) |
| *C12Q 1/6816* | (2018.01) |

(52) U.S. Cl.
CPC .......... *A61K 38/465* (2013.01); *A61K 9/0048* (2013.01); *A61K 31/465* (2013.01); *A61K 45/05* (2013.01); *A61K 45/06* (2013.01); *C12Q 1/6816* (2013.01); *C12Y 301/21001* (2013.01)

(58) Field of Classification Search
None
See application file for complete search history.

(56) References Cited

U.S. PATENT DOCUMENTS

| | | | |
|---|---|---|---|
| 6,759,040 B1 * | 7/2004 | Manyak | A61L 2/186 424/94.2 |
| 7,479,481 B2 | 1/2009 | Molina | |
| 2004/0131626 A1 | 7/2004 | Goldstein | |
| 2005/0255144 A1 | 11/2005 | Schultz | |
| 2008/0096817 A1 | 4/2008 | Goldstein | |

(Continued)

FOREIGN PATENT DOCUMENTS

| | | |
|---|---|---|
| CN | 101195025 | 6/2008 |
| WO | 89/12689 | 12/1989 |

(Continued)

OTHER PUBLICATIONS

Whitchurch, Cynthia B; et al; "Extracellular DNA Required for Bacterial Biofilm Formation" Science, 295, 1487, 2002 (Year: 2002).*

(Continued)

*Primary Examiner* — David W Berke-Schlessel
(74) *Attorney, Agent, or Firm* — Michael Best & Friedrich LLP

(57) ABSTRACT

Provided herein is a composition and a method for treating nucleic acid-related eye disease.

10 Claims, 16 Drawing Sheets
Specification includes a Sequence Listing.

(56) References Cited

U.S. PATENT DOCUMENTS

| | | | |
|---|---|---|---|
| 2008/0139545 A1* | 6/2008 | Choe | A61K 31/497 514/230.2 |
| 2008/0199509 A1* | 8/2008 | Nick | A01N 37/46 424/423 |
| 2008/0233053 A1 | 9/2008 | Gross et al. | |
| 2009/0131449 A1 | 5/2009 | Yanni et al. | |
| 2009/0312724 A1 | 12/2009 | Pipkin et al. | |

FOREIGN PATENT DOCUMENTS

| | | |
|---|---|---|
| WO | 1999/006022 | 2/1999 |
| WO | 2005/115432 | 12/2005 |
| WO | 2009-002790 | 12/2008 |
| WO | WO-2011098579 A1 * | 8/2011 ............. A61L 29/16 |

OTHER PUBLICATIONS

Korean Patent Office Action for Application No. 10-2014-7019155 dated Nov. 15, 2017 (12 pages, English translation included).
Canadian Patent Office Action for Application No. 2,858,983 dated Dec. 1, 2017 (5 pages).
Russian Patent Office Action for Application No. 2014128564 dated Apr. 25, 2017 (5 pages including English translation).
Chinese Patent Office Action for Application No. 201280069247.8 dated Apr. 28, 2017 (9 pages including English translation).
Australian Patent Office Examination Report for Application No. 2012352983 dated Apr. 7, 2017 (4 pages).
Yusifov et al., "Tear lipocalin is the major endonuclease in tears," Molecular Vision, 2008: 14: 180-188.
Yamada et al., "Decreased tear lipocalin concentration in patients with meibomian gland dysfunction," Br. J. Ophthalmol. 2005; 89:803-805.
Fujihara et al., "Lactoferrin Suppresses Loss of Corneal Epithelial Integrity in a Rabbit Short-Term Dry Eye Model," Journal of Ocular Pharmacology, vol. 14(2), 1998, pp. 1-9.
Babina et al., "Lactoferrin Is the Major Deoxyribonuclease of Human Milk," Biochemistry (Moscow), vol. 69(9), 2004, 1006-1015.
Huang et al., "Investigation of Tear Film Change After Recovery From Acute Conjunctivitis" Cornea, 26(7), Aug. 2007, 778-781.
Third Party Submission in European Patent Office Application No. 12858050.3 dated Oct. 14, 2016 (6 pages).
United States Patent Office Notice of Allowance for U.S. Appl. No. 14/362,589 dated Jul. 19, 2017 (8 pages).
Barliya et al., Molecular Vision, "Possible involvement of NETosis in inflammatory processes in the eye: Evidence from a small cohort of patients," 23: 922-932 (2017).
PCT International Search Report and Written Opinion for Application No. PCT/US2012/051562 dated Feb. 28, 2013 (13 pages).
Chinese Patent Office Action for Application No. 201280069247-8 dated May 29, 2015 (9 pages, statement of relevance included).
European Patent Office Extended Search Report for Application No. 12858050.3 dated Aug. 10, 2015 (7 pages).
Chinese Patent Office Action for Application No. 201280069247-8 dated Feb. 6, 2016 (7 pages, statement of relevance included).
Chinese Patent Office Action for Application No. 201280069247-8 dated May 9, 2016 (6 pages, statement of relevance included).
Japanese Patent Office Action for Application No. 2014-547214 dated May 24, 2016 (9 pages).
Russian Patent Office Action for Application No. 2014128564 dated May 19, 2016 (7 pages including translation).
Russian Patent Office Action for Application No. 2014128564 dated Aug. 26, 2016 (6 pages including translation).
Australian Patent Office Exam Report for Application No. 201235983 dated Oct. 18, 2016 (3 pages).
Sonawane, Snehal; et al; "Ocular Surface Extracellular DNA and Nuclease Activity Imbalance: A New Paradigm for Inflammation in Dry Eye Disease" Investigative Ophthalmology & Visual Science, 53, 8253-8263, 2012.
United States Patent Office Action for U.S. Appl. No. 14/362,589 dated Nov. 4, 2015 (8 Pages).
Japanese Patent Office Action for Application No. 2014-547214 dated Dec. 6, 2016 (4 pages).
Russian Patent Office Action for Application No. 2014128564 dated Dec. 23, 2016 (6 pages including translation).
European Patent Office Examination Report for Application No. 12858050.3 dated Dec. 20, 2016 (7 pages).
United States Patent Office Action for U.S. Appl. No. 14/362,589 dated Mar. 17, 2017 (8 Pages).
United States Patent Office Notice of Allowance for U.S. Appl. No. 14/362,589 dated Oct. 5, 2016 (8 Pages).
United States Patent Office Notice of Allowance for U.S. Appl. No. 14/362,589 dated Jun. 8, 2016 (9 Pages).
Apostolov et al., "Deoxyribonuclease I is Essential for DNA Fragmentation Induced by Gamma Radiation in Mice," Radiat Res. Oct. 2009 ; 172(4): 481-492.
Basnakian et al., "Cisplatin Nephrotoxicity Is Mediated by Deoxyribonuclease I," J Am Soc Nephrol 2005, 16: 697-702.
Napirei et al., "Deoxyribonuclease 1 Aggravates Acetaminophen-Induced Liver Necrosis in Male CD-1 Mice," Hepatology, 2006, vol. 43: 297-305.
Nitahara et al., "Intracellular Calcium, DNase Activity and Myocyte Apoptosis in Aging Fischer 344 Rats," J Mol Cell Cardiol (1998) 30, 519-535.
Oliveri et al. "DNase I behaves as a transcription factor which modulates Fas expression in human cells," Eur. J. Immunol. 2004. 34: 273-279.

* cited by examiner

A.                                    B.

COMPOSITION AND METHOD FOR TREATING NUCLEIC ACID-RELATED EYE DISEASE

CROSS-REFERENCE TO RELATED APPLICATIONS

This is a divisional of U.S. patent application Ser. No. 14/362,589, filed on Aug. 27, 2014, which is a U.S. national stage entry of International Patent Application No. PCT/US2012/051562, filed on Aug. 20, 2012, which claims priority to U.S. Provisional Patent Application No. 61/600,377, filed on Feb. 17, 2012, and U.S. Provisional Patent Application No. 61/569,604, filed on Dec. 12, 2011, the entire contents of all of which are fully incorporated herein by reference.

BRIEF DESCRIPTION OF SEQUENCE LISTING

This application includes a sequence listing in accordance with 37 C.F.R. §§ 1.821-1.825. The sequence listing is contained in a file named "DF055-PCT-US-DIV-092334-9007-US03-SEQ-LIST-01-03-17.txt" (833 bytes, created on Sep. 14, 2016) and it is hereby incorporated by reference.

FIELD OF THE INVENTION

The present invention relates to a composition and method for treating nucleic acid-related eye disease.

BACKGROUND

The ocular surface epithelium undergoes continuous, dynamic turnover, which is part of a normal shedding process. This turnover is increased in subjects suffering from various forms of nucleic acid-related eye disease, such as dry eye disease (DED). Superficial corneal cells are shed into the precorneal tear film. The corneal epithelial cell shedding process, or desquamation, is regulated by apoptotic mechanisms. Dead and dying cells release nucleic acid, a type of damage-associated molecular pattern molecule, which can stimulate the innate immune system and link it to adaptive immune system. Extracellular DNA strands, for example, have been reported in corneal filaments, which are frequently present on the corneas of patients with DED. Desquamated cells in the precorneal tear film are a potential source of extracellular DNA. Tear fluid contains several neutrophil extracellular trap (NET) components. Neutrophils undergo a low level of recruitment on the ocular surface, and numerous neutrophils are present in the tear film during ocular surface inflammation, which has a prominent role in symptom development and amplification. Neutrophil elastase and histone proteins have also been reported in tear fluid. These reports document the presence of extracellular DNA, histones, neutrophils, neutrophil elastase, and nucleases in tear fluid and perhaps suggest mechanisms exist for the continual production and clearance of extracellular DNA in tear film.

Extracellular DNA in tear film, such as ocular biofilm and mucoid film, may play a role in the pathology associated with nucleic acid-related eye disease. Nucleic acid-related eye diseases that may be associated with the formation of ocular mucoid films and/or biofilms present potentially disabling conditions, which adversely impact the vision-related quality of life. They can lead to ocular discomfort and/or deterioration in visual performance, such as reading speed and contrast sensitivity.

Despite the high incidence of nucleic acid-related eye diseases, there is currently no consistently effective treatment for these conditions. Because hyperosmolarity and inflammation have traditionally been thought as central reasons for dry eye disease, for example, current treatments focus on the use of eye-lid hygiene, topical antibiotics, oral tetracyclines, anti-inflammatories and/or corticosteroids. Such treatments are often ineffective or variably effective. As such there is a need for new therapeutic modalities to treat nucleic acid-related eye diseases, such as DED, that can result from the production/formation of nucleic acid in conjunction with ocular mucoid films and/or biofilms, for example.

SUMMARY OF THE INVENTION

Provided herein is a composition for the treatment of nucleic acid-related eye diseases. These diseases may be associated with poor tear quality, which may be related to nucleic acid biofilm/mucoid film formation on the surface of the eye or inside the eye. The nucleic acid may be extracellular. One such disease is dry eye disease (DED). The composition may comprise nuclease and an ophthalmic excipient. The nuclease may be a DNase or an RNase, or a combination thereof. The nuclease may be an endonuclease or an exonuclease. The DNase may be Deoxyribonuclease I (DNase I); Deoxyribonuclease II (DNase II); Deoxyribonuclease III, or a micrococcal nuclease. The RNase may be Ribonuclease A (RNase A); Ribonuclease H (RNase H); Ribonuclease I (RNase I); Ribonuclease II (RNase II); Ribonuclease III (RNase III); Ribonuclease D (RNase D); Ribonuclease L (RNase L); Ribonuclease P (RNase P); Ribonuclease PH (RNase PH); Ribonuclease PhyM (RNase PhyM); Ribonuclease R (RNase R); Ribonuclease T (RNase T); Ribonuclease T1 (RNase T1); Ribonuclease T2 (RNase T2); Ribonuclease U2 (RNase U2); Ribonuclease V1 (RNase V1); Ribonuclease V (RNase V); Oligoribonuclease; Exoribonuclease I; or Exoribonulcease II. The DNase or RNase may be recombinant. The composition may further comprise an antagonist or inhibitor. The antagonist or inhibitor may be selected from the group consisting of an antibiotic compound, toll-like receptor antagonist, type-1 interferon antagonist, cathelicidin inhibitor, a MyD88 inhibitor, a steroid, an anti-allergy compound, and a neutrophil elastase inhibitor, and combinations thereof.

Also provided herein is a method for treating a nuclease-related eye disease. The method may comprise administering the above-described nuclease composition with an ophthalmic excipient to the eye in an amount effective to treat the eye disease. The ocular surface of the eye may contain a tear film, which may be a biofilm or a mucoid film. The biofilm or mucoid film may contain nucleic acid. The nucleic acid may be extracellular nucleic acid. The nucleic acid may be DNA, RNA, or a combination thereof. The tear film may contain less than 3.14 ng/ml of nuclease prior to administering the composition. The tear film may contain less than 0.05 Kunitz units of nuclease activity prior to administering the composition. An effective amount of the composition may contain between 5 ng/ml and 3 mg/ml of the nuclease. An effective amount of the composition may contain between 100 ng/ml and 200 ng/ml of the nuclease.

The nucleic acid-related eye disease may be DED, diffuse lamellar keratitis, contact lens-associated keratitis, endophthalmitis, or infectious crystalline keratopathy, ocular cicatricial pemphigoid (OCP), keratoconjunctivitis sicca (KCS), Sjogren syndrome (SS), Sjogren syndrome associated keratoconjunctivitis sicca, non-Sjogren syndrome associated keratoconjunctivitis sicca, keratitis sicca, sicca syndrome, xerophthalmia, tear film disorder, decreased tear production, aqueous tear deficiency (ATD), or meibomian gland dysfunction (MGD). DED may be an autoimmune DED or a DED associated with Sjorgren's syndrome, for example. The DED may be attributable to one or more causes including: aging, contact lens usage and medication usage. The antibiotic may be ampicillin, amoxicillin/clavulanate, metronidazole, clindamycin, erythromycin, gentamicin, vancomycin, ciproflaxin, clindamycin, tetracycline, an anxiolytic, or a combination thereof. The toll-like receptor antagonist may be an oligonucleotide comprising the sequence TTAGGG. The oligonucleotide may consist of the sequence TTAGGGTTAGGGTTAGGGTTAGGG (SEQ ID NO:1). The type-1 interferon antagonist may be any compound that antagonizes or competitively inhibits type I interferon binding to its receptor, such as receptor subunits IFNAR-1 and/or IFNR-2. The compound may be an anti-IFNα antibody. The cathelicidin inhibitor may be a bacterial exopolysaccharide. The neutrophil elastase inhibitor may be selected from the group consisting of ONO-5046, MR-889, L-694,458, CE-1037, GW-311616 TEI-8362, ONO-6818, AE-3763, FK-706, ICI-200,880, ZD-0892 and ZD-8321.

Also provided herein is a method for determining whether a subject has a nuclease-related eye disease. The method may comprise collecting a tear sample from a subject. This sample may be contacted with a dye that binds to DNA, such as picogreen. Alternatively, the sample may be contacted with a DNase and then contacted with the dye. The intensity of the color may be measured and compared to the intensity of dye fluorescence in a normal control sample. An increased level of dye fluorescence intensity in the sample as compared to the control may be indicative of a dry eye disease.

Also provided herein is a method for treating an ocular bacterial infection. The method comprises administering a composition comprising a nuclease to the eye in an amount effective to treat the infection. The composition may be injected into the eye.

BRIEF DESCRIPTION OF THE DRAWINGS

FIG. 3 shows the presence of extracellular DNA, which is important for the formation of NETs.

DETAILED DESCRIPTION

Figure 1:
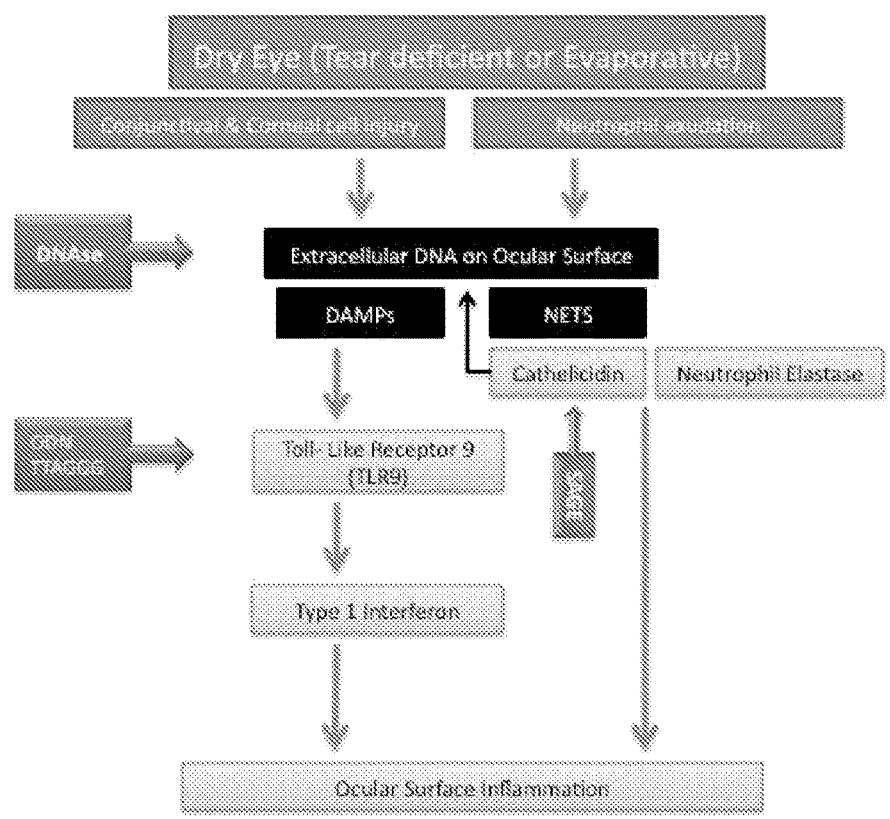
FIG. 1 shows a schematic of the biology of DED. Extracellular DNA is found on the ocular surface of eyes affected by DED. This extracellular DNA may come from two major sources: neutrophils and conjunctival and other corneal cells. Neutrophil extracellular DNA forms neutrophil extracellular traps (NETs). These NETs have inflammatory and angiogneic molecules, such as cathelicidin, neutrophil elastase, and histone associated with them. ExtracellularDNA from conjunctival cells, as well as in NETs, acts as "damaged associated molecule patterns" (DAMPS). DAMPs trigger and sustain inflammation. DNA DAMPS act via the toll-like receptor 9 (TLR9) to increase type 1 interferons, which increase the presence of several mediators of inflammation.
Figure 2:
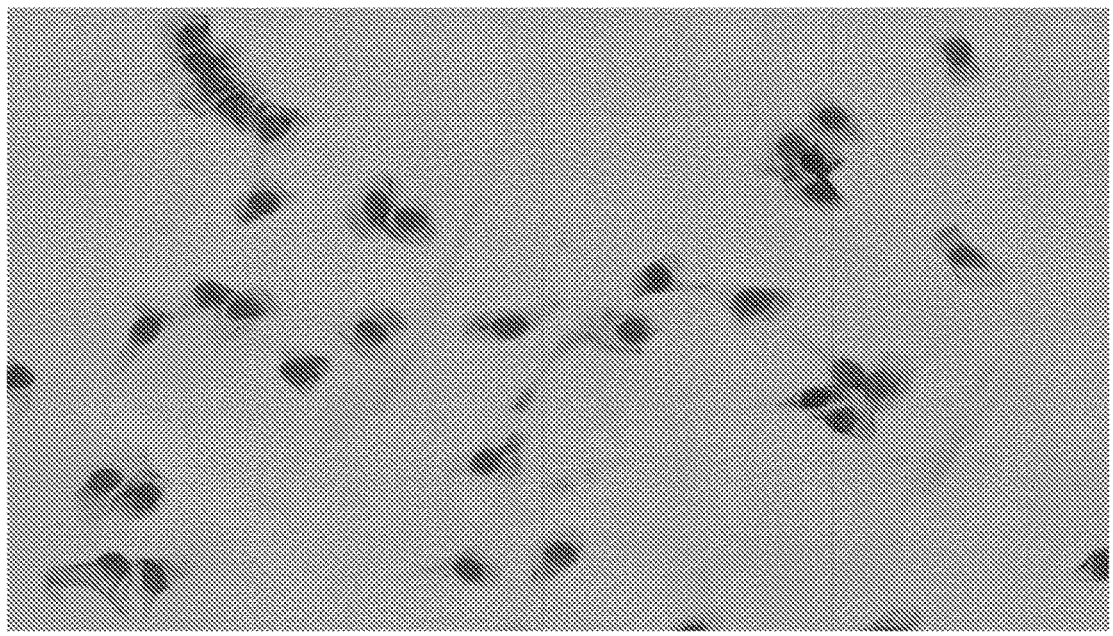
FIG. 2 shows cells transferred on silane coated adhesive slides and stained by hematoxylin and eosin. The nuclei and strands are stained by hematoxyline showing the presence of intracellular and extracellular DNA respectively, further indicating the presence of NETs.
Figure 3:
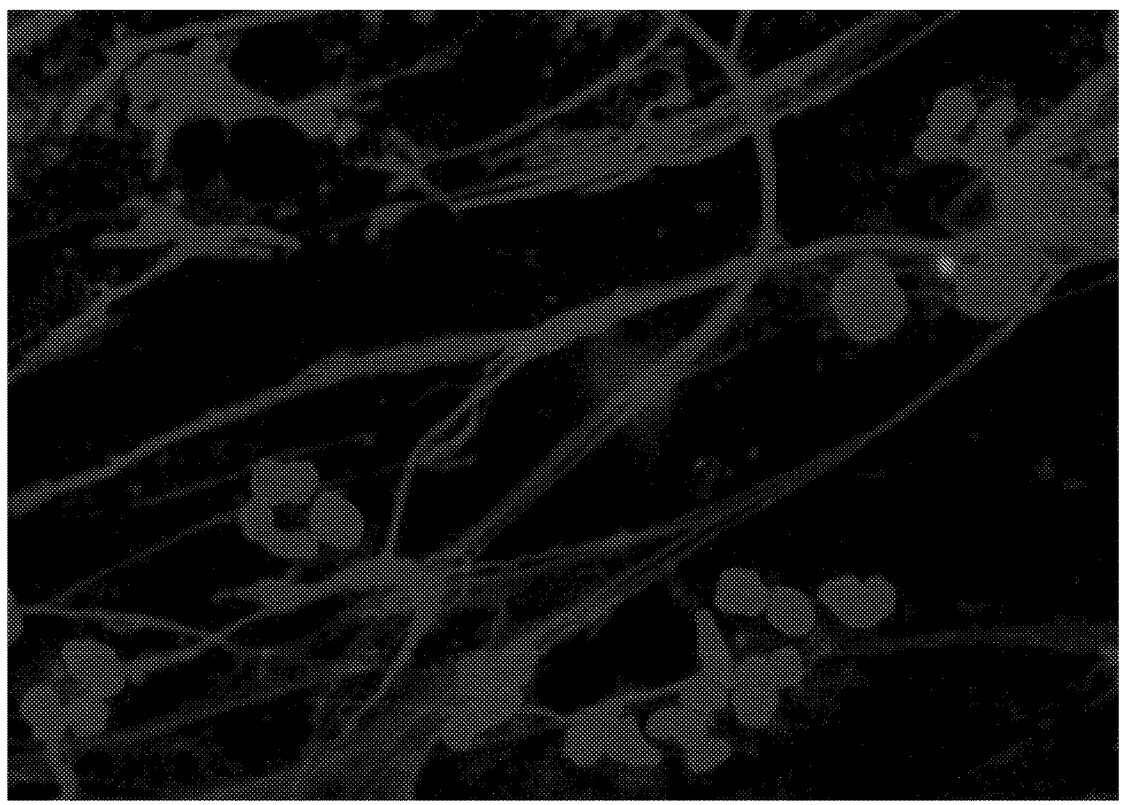
FIG. 3 shows a confocal image (63X) of indirect immunofluorescence stained with DAPI stain for nucleic acid. The stain is picked up by the cell nucleus as well as by extracellular DNA strands.
Figure 4:
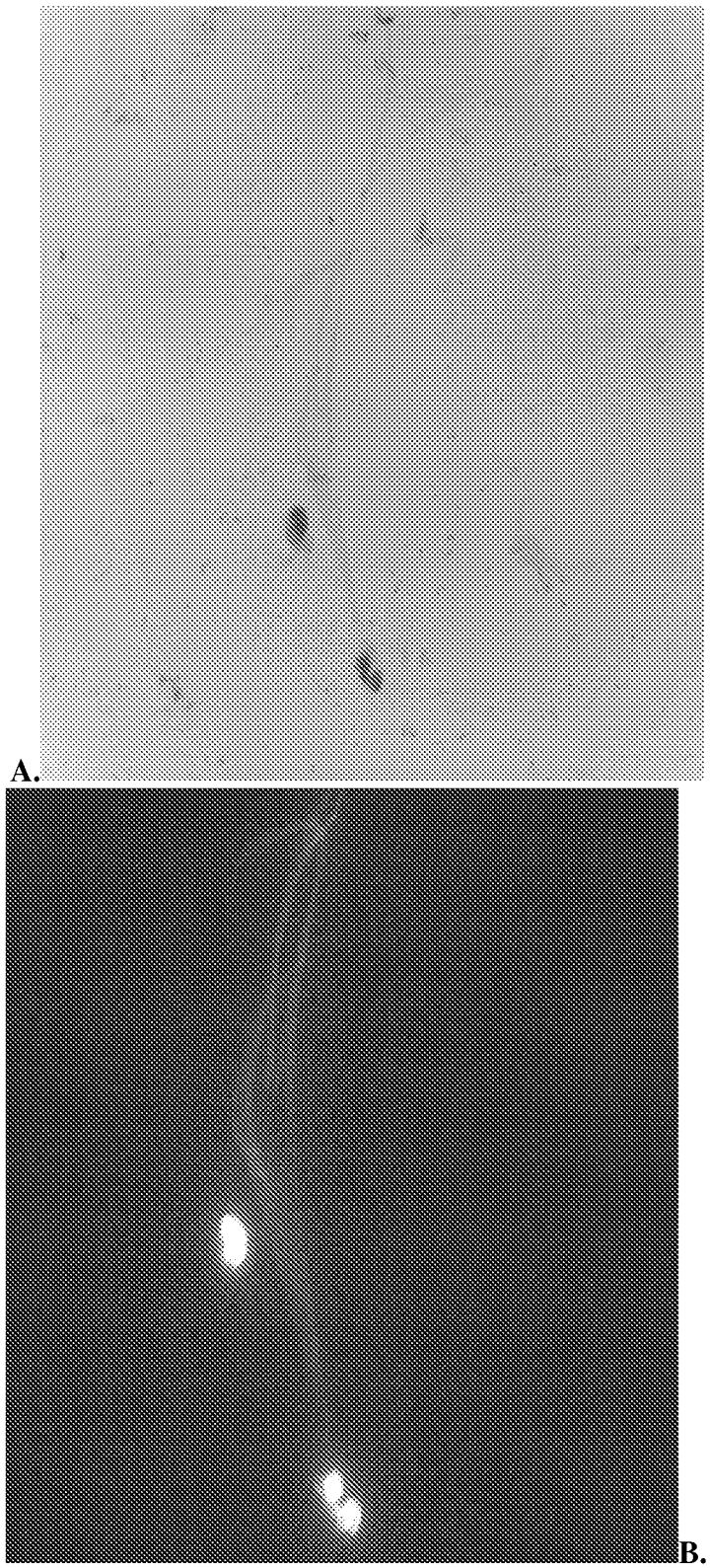
FIG. 4 shows the presence of neutrophils and strands coming out from cells as extracellular DNA. The cells were first stained with indirect immunofluorescence. (B) shows extracellular strand like structure revealing nuclear and extracellular DNA. The cells were then washed and stained with hematoxylin and eosin to confirm the presence of neutrophil and the strand coming out from the cell thereby confirming the presence of NETs.
Figure 5:
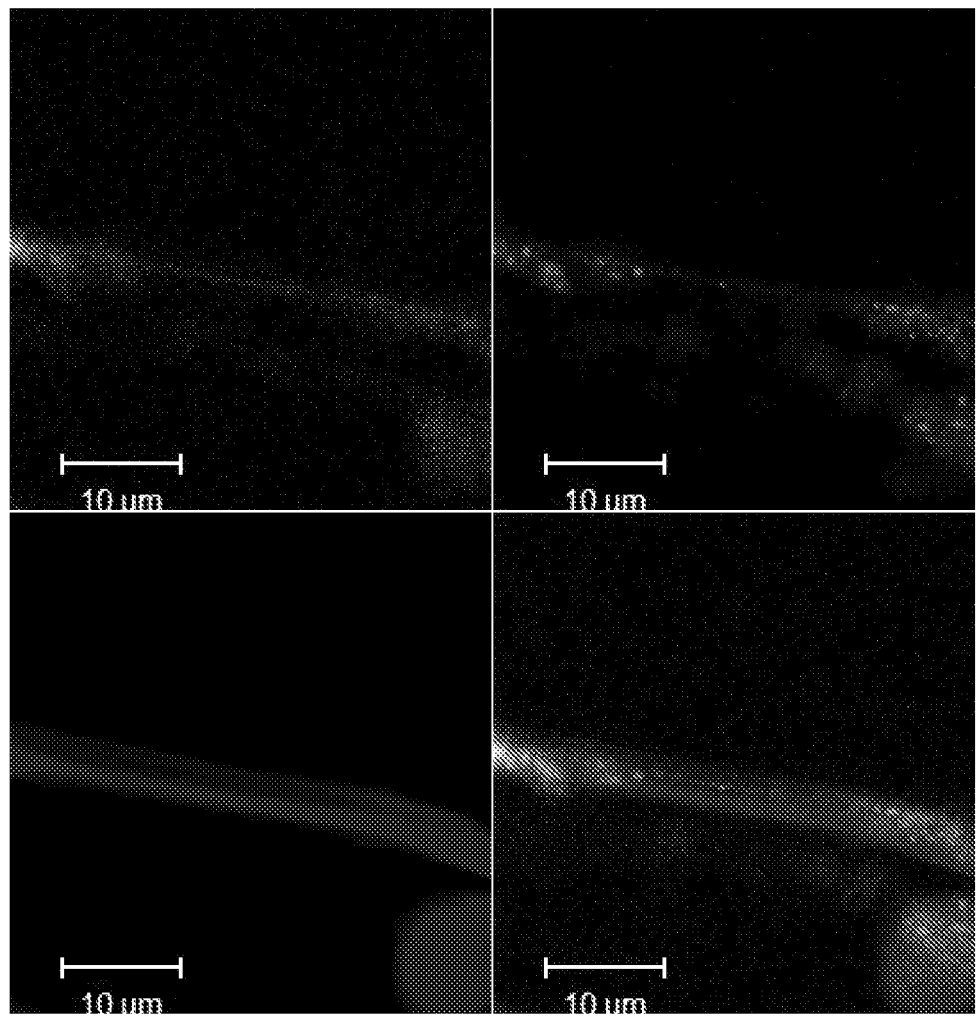
FIG. 5 shows a confocal image, whereby cells are indirectly immunofluoresced with primary antibody against neutrophil elastase, histone and DAPI. Granular staining for neutrophil elastase co-localizes with histone and nucleic acid.
Figure 6:
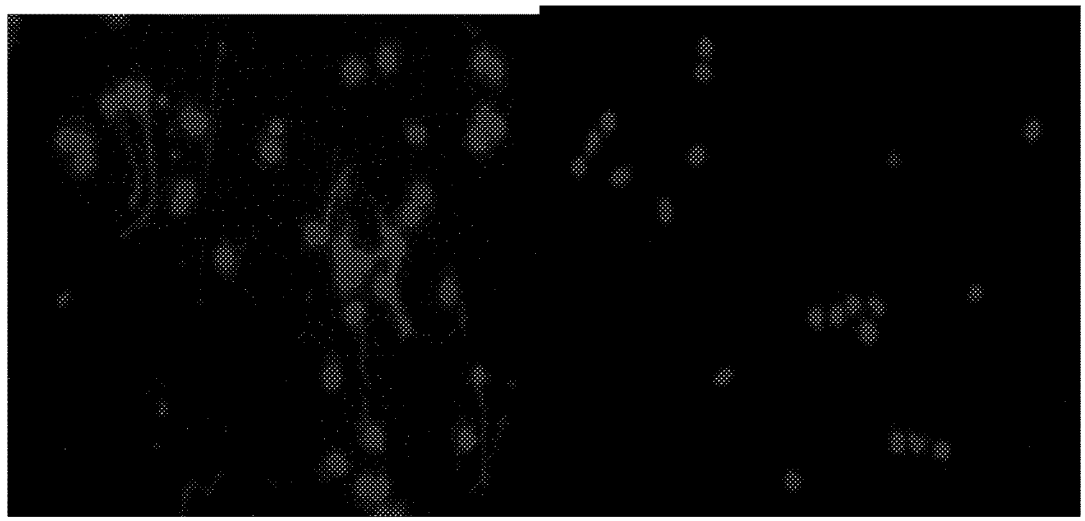
FIG. 6 shows the presence of NETs on the ocular surface (A). After treatment with DNase, stranded extracellular DNA disappears, while cellular integrity is maintained (B). The two samples (A) and (B) were collected from the same subject. Sample A was treated with PBS for 20 minutes then stained with DAPI. Sample B was treated with DNase (100 IU/ml) for 20 minutes and stained with DAPI.
Figure 7:
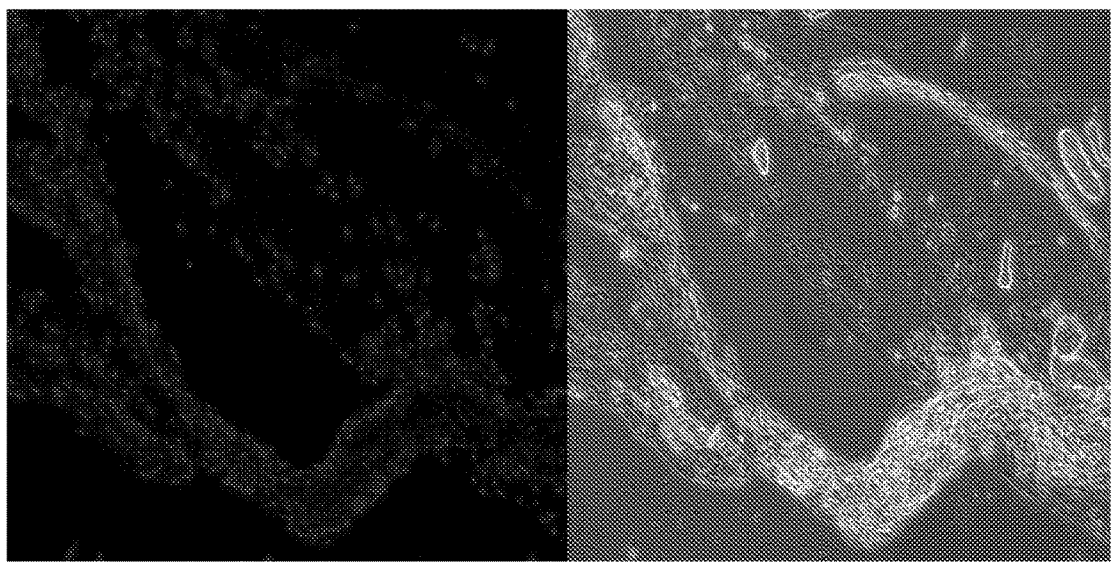
FIG. 7 show confirmation of the presence of NETs and differentiating them from mucous on the ocular surface. A specimen of mucous from the conjunctival surface was stained with DAPI. The nucleus was stained; however, the mucous was not stained.
Figure 8:
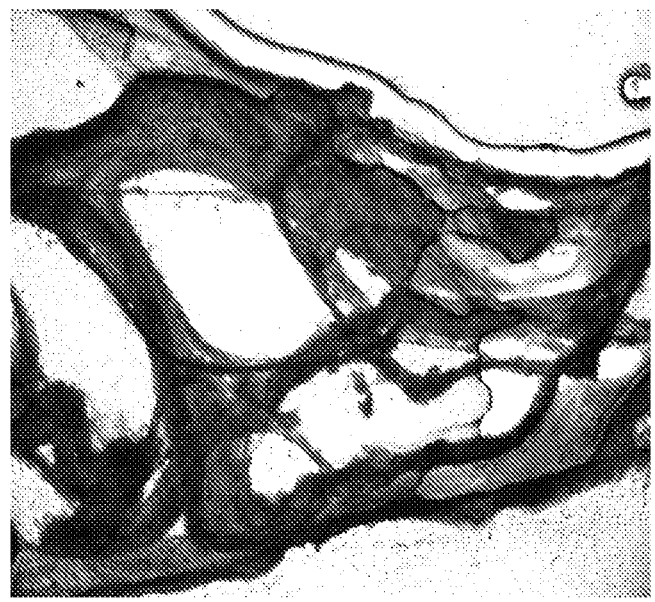
FIG. 8 further confirms the presence of mucous from the same subject from which the specimen was obtained in FIG. 7. The specimen was stained with Periodic Acid Schiff (PAS). The staining shows the presence of mucous strands.
Figure 9:
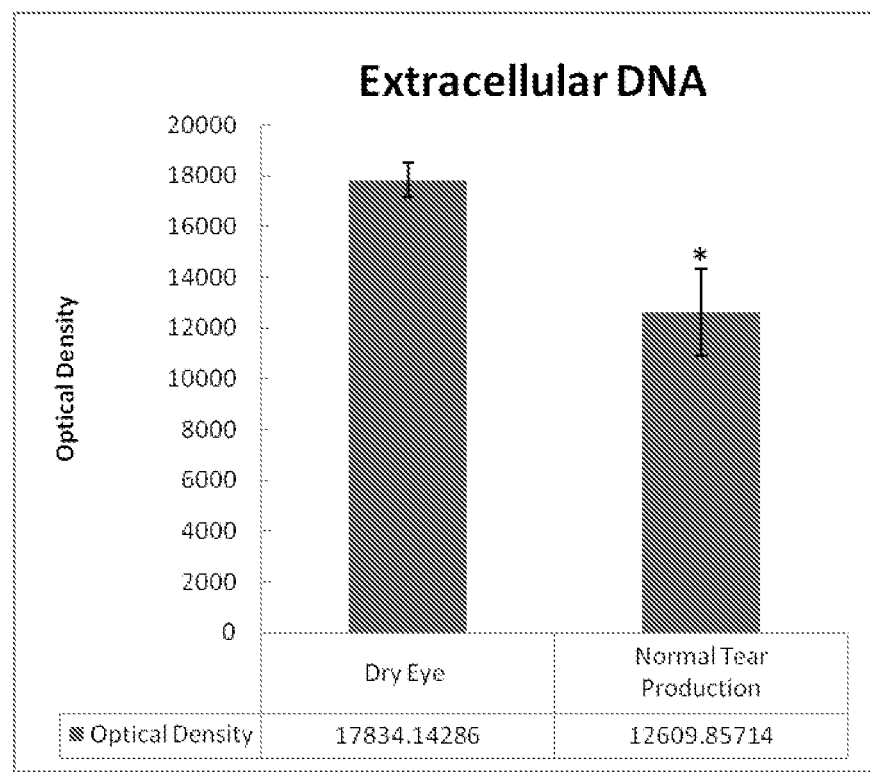
FIG. 9 shows a graph for dry eye (with Schirmer's Test <5) compared to normal tear production (with Schirmer's Test >5) with standard deviation in error bars. There is a significant difference between the optical density for extracellular DNA in dry eye disease compared to normal tear production. The optical density in dry eye is greater (17834.14) than in normal tear production (12609.86). Thus, in dry eye disease, the amount of extracellular DNA obtained from Schirmer's filter paper is greater compared to Schirmer's with normal tear production.
Figure 10:
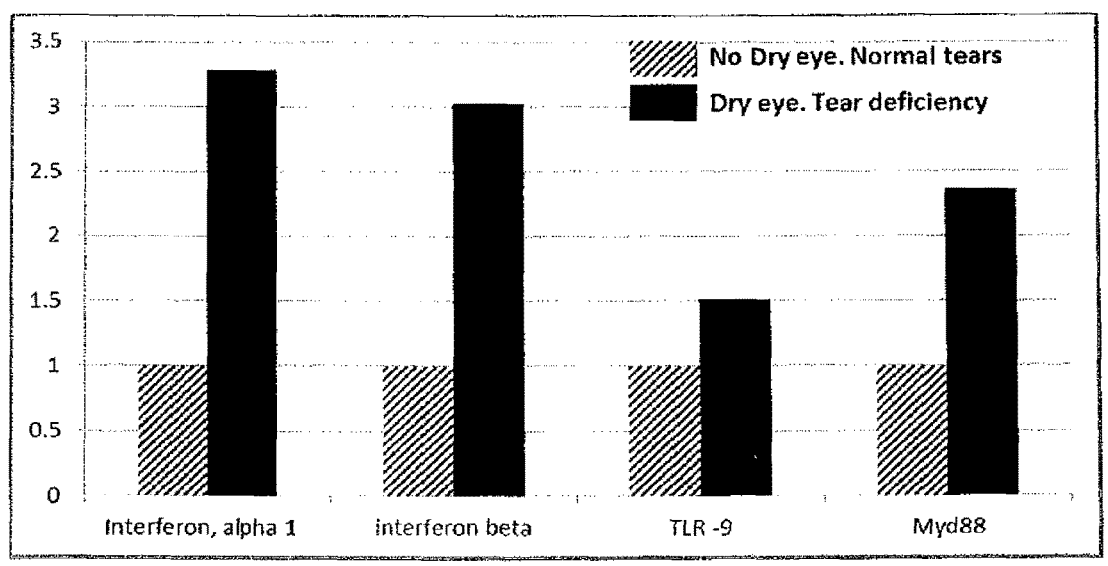
FIG. 10 shows quantitative real-time PCR data regarding the level of Interferon alpha 1, interferon beta, TLR-9, and Myd88 genes in humans with severe dry eye cells as compared to humans with normal tear production (no dry eye). The levels of these genes are several fold increased in the conjunctiva of patients with dry eyes and tear deficiency. These pathways (TLR-9 and Myd88) are stimulated by extracellular DNA, thus providing receptor and transcriptional data support for the stimulation of ocular surface inflammation by extracellular DNA. The downstream mediators of inflammation (interferon alpha and beta) are also increased in dry eye patients.

The inventors have made the surprising discovery that nucleic acid-related eye diseases, such as DED, and DED-related conditions, can be treated with a nuclease and an ophthalmic excipient in the presence or absence of an antibiotic. Central to this discovery is the presence of neutrophil extracellular traps (NETs) on the surface of the eye(s) in subjects who have a nucleic acid-related eye disease, such as DED. NETs are extracellular structures composed of chromatin, which includes nucleic acid, such as DNA; neutrophil elastase; histone; and granule proteins. NETs can provide local concentrations of antimicrobial activity and, accordingly, are prevalent at inflammatory sites.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

a. Control

"Control" as used herein may mean a composition or sample known to not have a dry eye disease or be bacterially infected (a negative control). A positive control may mean a sample that harbors a nucleic acid-related eye disease, or is bacterially infected. Any control may comprise a known amount of extracellular DNA.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Nuclease-Based Composition

Provided herein is a nuclease-based composition ("nuclease composition") that is capable of removing nucleic acid from the surface of the eye or inside the eye. The nucleic acid may be extracellular. The nuclease composition may contain one or more nucleases. The nuclease may be a DNase or an RNase. The nuclease composition may also contain an ophthalmic excipient. The nuclease composition may further contain one or more an antibiotic compound, anti-viral compound, an anti-inflammatory, a toll-like receptor antagonist, a type-1 interferon antagonist, a cathelicidin inhibitor, MyD88 inhibitor, steroid, anti-allergy compound, and/or a neutrophil elastase inhibitor. Alternatively, the nuclease composition may not contain any of an antibiotic compound, an anti-viral compound, an anti-inflammatory, a toll-like receptor antagonist, a type-1 interferon antagonist, a cathelicidin inhibitor, and/or a neutrophil elastase inhibitor, but rather may be used in combination with one or more of antibiotic compounds, toll-like receptor antagonists, type-1 interferon antagonists, cathelicidin inhibitors, and/or a neutrophil elastase inhibitors.

The pH and/or the osmolarity of the nuclease composition may be appropriately adjusted prior to use. The pH of the nuclease composition may be between 4 and 9, between 5 and 8, between 6 and 7, or between 6.5 and 7.5. The pH of the nuclease composition may be 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9. 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.9, or 9.0. The pH of the nuclease may be 7.4.

The osmolarity of the nuclease composition may be hypo-osmolar or iso-osmolar. For example the DNase composition may have an osmolarity of between 100 mOsm/liter and 500 mOsm/liter, 150 mOsm/liter and 450 mOsm/liter, 200 mOsm/liter and 400 mOsm/liter, 250 mOsm/liter and 350 mOsm/liter, 275 mOsm/liter and 325 mOsm/liter, 100 mOsm/liter and 150 mOsm/liter, 150 mOsm/liter and 200 mOsm/liter, 150 mOsm/liter and 300 mOsm/liter, 200 mOsm/liter and 300 mOsm/liter, 0 mOsm/liter and 100 mOsm/liter, 25 mOsm/liter and 75 mOsm/liter, 50 mOsm/liter and 125 mOsm/liter, or between 0 mOsm/liter and 50 mOsm/liter.

a. Nuclease

The nucleases contemplated in the present invention include DNases and RNases.

The DNase may be any enzyme that catalyzes the hydrolytic cleavage of phosphodiester linkages in a DNA backbone. One such enzyme is a deoxyribonuclease. Examples of deoxyribonucleases include, but are not limited to: Deoxyribonuclease I (DNase I); Deoxyribonuclease II (DNase II); and micrococcal nuclease. The DNase may be recombinant human DNase or an animal sourced form (e.g. bovine) or a microbial sourced form. The recombinant DNase I may be dornase alpha, which is available under the tradename PULMOZYME® from Genentech, Inc. A DNase variant may be created by modifying its genetic composition, for example, by removing the signal peptide, mutating substrate binding sites or amino acid substitutions to create hyperactive variants or more stable variants. For example, DNase II or DNase-like I, II, or III their variants may be used, either in combination or alone.

The RNase may be any enzyme that catalyzes the hydrolytic cleavage of phosphodiester linkages in an RNA backbone. One such enzyme is a ribonuclease. Examples of ribonucleases include, but are not limited to: Ribonuclease A (RNase A); Ribonuclease H (RNase H); Ribonuclease I (RNase I); Ribonuclease II (RNase II); Ribonuclease III (RNase III); Ribonuclease D (RNase D); Ribonuclease L (RNase L); Ribonuclease P (RNase P); Ribonuclease PH (RNase PH); Ribonuclease PhyM (RNase PhyM); Ribonuclease R (RNase R); Ribonuclease T (RNase T); Ribonuclease T1 (RNase T1); Ribonuclease T2 (RNase T2); Ribonuclease U2 (RNase U2); Ribonuclease V1 (RNase V1); Ribonuclease V (RNase V); Oligoribonuclease; Exoribonuclease I; and Exoribonulcease II. The RNase may be recombinant human RNase or an animal or microbial sourced form (e.g. bovine). An RNase variant may be created by modifying its genetic composition, for example, by removing the signal peptide, mutating substrate binding sites or amino acid substitutions to create hyperactive variants or more stable variants.

The nuclease may cleave only residues at the ends of nucleic acid molecules (exodeoxyribonucleases or exoribonucleases, types of exonucleases). The nuclease may be an endonuclease, which may be used alone or in combination with another nuclease. Examples of endonucleases are lipocalin and RNase A. The nuclease may cleave anywhere along the chain (endodeoxyribonucleases or endoribonucleases, subsets of endonucleases). The nuclease may be indiscriminate about the DNA sequence at which it cuts. The nuclease may be sequence-specific. The nuclease may cleave only double-stranded nucleic acid, only single-stranded nucleic acid, or both double-stranded and single stranded nucleic acid.

The nuclease dosage may be determined by a doctor, for example, without undue experimentation. The dosage can be adjusted in the event of any counter indications, tolerance, or similar conditions. Those of skill in the art can readily evaluate such factors and, based on this information, determine a particular effective concentration of the nuclease to be used as described herein. The nuclease may be present in the nuclease composition at between 5 ng/ml and 3 mg/ml, between 1 mg/ml and 3 mg/ml, between 2 mg/ml and 3 mg/ml, between 10 ng/ml and 900 ng/ml, between 20 ng/ml and 800 ng/ml, between 30 ng/ml and 700 ng/ml, between 40 ng/ml and 600 ng/ml, between 50 ng/ml and 600 ng/ml, between 60 ng/ml and 500 ng/ml, between 70 ng/ml and 400 ng/ml, between 80 ng/ml and 300 ng/ml, between 90 ng/ml and 200 ng/ml, between 50 ng/ml and 250 ng/ml, between 100 ng/ml and 200 ng/ml, between 150 ng/ml and 250 ng/ml, between 100 ng/ml and 150 ng/ml, or between 90 ng/ml and 100 ng/ml. The nuclease may be present in the nuclease composition at 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 110 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1 mg/ml, 2, mg/ml, or 3 mg/ml. As described in more detail herein, the composition may be manually delivered to the eye in suitable dosage form, e.g., eye drops, or delivered by suitable microdrop or spray apparatus typically affording a metered dose of medicament.

(1) Ophthalmic Excipient

The ophthalmic excipient may be any ophthalmic excipient. The ophthalmic excipient may be a buffer, tonicity adjuster, wetting agent, and/or an antioxidant. The buffer may be boric and/or phosphoric acid. The buffer may minimize changes to the pH of the nuclease composition. The tonicity adjuster may provide an isotonic environment and may include sodium chloride, potassium chloride, magnesium chloride, and/or boric acid. Antioxidants include sodium metabisulfite and EDTA, for example. The antioxidants may be used to help stabilize the nuclease composition. Wetting agents, which include polyvinyl alcohol (PVA) and polysorbate 80, may allow the nuclease composition to spread over the eye. Other ophthalmic excipients include benzalkonium chloride (BAK), ethylenediaminetetraacetic acid (EDTA), purite, chlorobutanol, sodium perborate and sorbic acid, sodium perborate, purite, polyols, glycerin, polysorbate 80, dextran 70, propylene glycol, and polyethylene glycols, such as PEG-400. The ophthalmic excipient may be an ointment, such as mineral oil, white petrolatum, white ointment or lanolin. Similar to the aqueous vehicles, petrolatum and mineral oil may serve as vehicles in the ointment formulations to increase ocular contact time. These ingredients may help to form an occlusive film over the surface of the eyeball and improve the composition of the tear film by enhancing the mucin and aqueous layers. The ophthalmic excipient may provide mucin-like properties and/or decrease the loss of the aqueous layer due to evaporation. The ophthalmic excipient may function as a carrier, such as a pharmaceutically acceptable carrier as described below.

(2) Antibiotic

The antibiotic may be any antibiotic. The antibiotic may be ampicillin, amoxicillin/clavulanate, metronidazole, clindamycin, erythromycin, gentamicin, vancomycin, ciproflaxin, clindamycin, tetracycline, an anxiolytic, amikacin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, doxycycline, or oxytetracycline. The antibiotic may be an ophthalmically-acceptable antibiotic.

(3) Antiviral

The antiviral compound may be any antiviral. The antiviral compound may be abacavir, acyclovir, adefovir, amantadine, amprenavir, ampligen, arbidol, atazanavir, atripla, boceprevir, cidofovir, darunavir, delavirdine, didanosine, docosanol, edoxudine, efavirenz, emtricitabine, enfuvirtide, entecavir, famcyclovir, fomivirsen, fosamprenavir, gancyclovir, ibacitabine, imunovir, idoxuridine, imiquimod, indinavir, lamivudine, lopinavir, loviride, maraviroc, moroxydine, pencyclovir, peremivir, pleconaril, ribavirin, ritonavir, saquinavir, telaprevir, tenofovir, truvada, valacyclovir, valgancyclovir, or zanamivir. The antiviral may be an ophthalmically-acceptable antiviral.

(4) Anti-Inflammatory

The anti-inflammatory may be a non-steroidal or steroidal anti-inflammatory. The anti-inflammatory may be cyclosporine or cyclosporine A. The cyclosporine A may be a 0.05% concentration of cyclosporine A (for example, RESTASIS®). The anti-inflammatory may be an ophthalmically-acceptable anti-inflammatory.

(5) Toll-Like Receptor-9 Antagonist

Toll-like receptor 9 (TLR9) recognizes specific unmethylated CpG oligonucleotide (ODN) sequences that distinguish microbial DNA from mammalian DNA. The toll-like receptor antagonist may be any oligonucleotide that can neutralize the stimulatory effect of CpG ODNs. These oligonucleotides may be characterized by three consecutive Gs downstream of a C or A. Further, the addition of a fourth G (G-tetrads) may increase the inhibitory capability of the ODN. The most potent inhibitory sequences are sequences that contain TTAGGG, for example (TTAGGG)$_4$ (SEQ ID NO:1). See FIG. 1, for example. The antagonist oligonucleotide may act by disrupting the colocalization of CpG ODNs with TLR9, such as in endosomal vesicles. The toll-like receptor-9 antagonist may be an ophthalmically-acceptable toll-like receptor-9 antagonist.

(6) Type-1 Interferon Antagonist

Type 1 interferon is part of a defensive response to viral infections and some intracellular parasites. While these proteins have therapeutic use against some viral diseases, tumors and multiple sclerosis. Type 1 interferons can be inappropriately produced in certain disease states.

The type-1 interferon antagonist may be any compound that antagonizes or competitively inhibits type I interferon. The compound may be an anti-interferon α antibody, for example. The compound may antagonize or inhibit type 1 interferon binding to its receptor. The compound may antagonize or inhibit type 1 interferon binding to its receptor subunits, IFNAE-1 or IFNR-2. The antagonist or competitive inhibitor can block the biological activity of native interferon. The type-1 interferon antagonist may be an ophthalmically-acceptable type-1 interferon antagonist.

(7) Cathelicidin Inhibitor

The cathelicidin inhibitor may be any inhibitor capable of blocking or decreasing the biological activity of cathelicidin, which can stabilize extracellular DNA on the ocular surface of eyes. An example of a cathelicidin inhibitor is bacterial exopolysaccharide. The cathelicidin inhibitor may be an ophthalmically-acceptable cathelicidin inhibitor.

(8) MyD88 Inhibitor

The MyD88 inhibitor may be any compound that can inhibit or decrease the biological activity or expression of MyD88. The MyD88 inhibitor may be a peptide or small molecule that inhibits MyD88 homodimerization, such as ST2825 (Sigma Tau, Pomezia, Italy), the synthetic oligopeptide IMG2205 (Imgenex Corporation, San Diego, Calif.), and/or MyD88 Inhibitory Peptide (MIP). The MyD88 inhibitor may inhibit MyD88 binding to signaling partners. The MyD88 inhibitor may be a dominant negative MyD88 protein. The MyD88 inhibitor may be an antisense, siRNA, or a shRNA molecule that inhibits MyD88 expression.

(9) Neutrophil Elastase Inhibitor

The neutrophil elastase inhibitor may be any compound that can inhibit or decrease the biological activity of neutrophil elastase, which is a serine protease secreted by neutrophils during inflammation. For example, the inhibitor may be synthetic, natural, reversible or irreversible. For example, the neutrophil elastase inhibitor may be ONO-5046, MR-889, L-694,458, CE-1037, GW-311616 or TEI-8362. The neutrophil elastase inhibitor may be ONO-6818, AE-3763, FK-706, ICI-200,880, ZD-0892 or ZD-8321. See, for example, Expert Opinion on Investigational Drugs, July 2002, Vol. 11, No. 7: Pages 965-980 (Neutrophil elastase inhibitors as treatment for COPD, by Hiroyuki Ohbayashi). The neutrophil elastase inhibitor may be an ophthalmically-acceptable neutrophil elastase inhibitor.

b. Pharmaceutically Acceptable Carrier

The nuclease compound can be incorporated into pharmaceutical compositions suitable for administration to a subject (such as a patient, which can be a human or non-human). Typically, the nuclease composition comprises a pharmaceutically acceptable carrier suitable for ophthalmic delivery. Suitable ophthalmic carriers are known to those skilled in the art and all such conventional carriers may be employed in the present invention. Suitable carriers that may be used to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist.

Optionally, the composition further contains a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum. Moreover, topically-administered compositions may comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine and EDTA. The solutions are preferably maintained at substantially neutral pH and isotonic with appropriate amounts of conventional buffers, e.g., phosphate, borate, acetate, tris.

Pharmaceutically acceptable ophthalmic carriers may further comprise amounts of auxiliary substances such as wetting or emulsifying agents, preservatives or buffers, which may enhance the shelf life or effectiveness of the nuclease, antibiotic compounds, anti-viral compounds, toll-like receptor antagonists, type-1 interferon antagonists, cathelicidin inhibitors, and/or a neutrophil elastase inhibitors.

Various delivery systems are known and can be used to administer the herein described compositions useful for treating or ameliorating a nucleic acid-related eye disease or one or more symptoms thereof, e.g., encapsulation in liposomes, microparticles, microcapsules. The composition may be administered via injection. For example, the composition may be injected into the eye. The nuclease composition may be in the form of liquid eye drops, a gel, or ointment, which may be applied directly to the ocular surface of the affected eye(s). The drops, gel, or ointment may be applied in accordance with instructions from a doctor and/or in accordance with dosage recommendations. For example, one drop of a composition containing between 100 ng/ml and 200 ng/ml of nuclease may be administered between 1 and 10 times daily between 1 and 7 times daily, between 1 and 4 times daily, or between 1 and 3 times daily.

The herein described nuclease composition may be delivered to the eye via contact lens. For example, the composition is incorporated into or coated onto said lens. The composition is chemically bound or physically entrapped by the contact lens polymer. Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of the invention include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, fluorofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyflufocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A.

Exemplary materials used to fabricate a hydrophilic lens with means to deliver the compositions of the invention include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A.

The composition may be administered as a solid, a paste, an ointment, a gel, a liquid, an aerosol, a mist, a polymer, a film, an emulsion, or a suspension. Furthermore, the composition may be incorporated into or coated onto a contact lens or drug delivery device, from which one or more molecules diffuse away from the lens or device or are released in a temporally-controlled manner. The contact lens composition may either remain on the ocular surface, e.g. if the lens is required for vision correction, or the contact lens dissolves as a function of time simultaneously releasing the composition into closely juxtaposed tissues. Similarly, the drug delivery device is optionally biodegradable or permanent in various embodiments.

In particular, one or more of the nuclease compositions, can be packaged in a hermetically sealed container such as an ampoule or sachette indicating the quantity of the nuclease, for example. In one embodiment, one or more of the nuclease compositions is/are supplied as a dry sterilized lyophilized powder or water-free concentrate in a hermetically sealed container and can be reconstituted (e.g., with water or saline) to the appropriate concentration for administration to a subject. In one embodiment, one or more of the compositions is supplied as a dry, sterile, lyophilized powder in a hermetically sealed container at a unit dosage of at least 0.01 mg, 0.05 mg, 0.1 mg, 0.25 mg, 0.5 mg, 1 mg, 1.5 mg, 2.0 mg, 5 mg, for example at least 10 mg, at least 15 mg, at least 25 mg, at least 35 mg, at least 45 mg, at least 50 mg, at least 75 mg, or at least 100 mg. The lyophilized compositions should be stored at between 2° C. and 8° C. in the original container and the compositions should be administered within 1 week, for example within 5 days, within 72 hours, within 48 hours, within 24 hours, within 12 hours, within 6 hours, within 5 hours, within 3 hours, or within 1 hour after being reconstituted. In a further embodiment, the liquid form of the administered nuclease composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The pharmaceutical compositions may include a "therapeutically effective amount" or a "prophylactically effective amount" of a nuclease. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the nuclease are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

c. Subject

The subject may be a mammal, which may be a human or a non-human. The subject may be in need of treatment for a nucleic acid-related eye disease.

3. Method of Treating a Nucleic Acid-Related Eye Disease

Provided herein is a method of treating a nucleic acid-related eye disease, such as DED. The nuclease composition may be contacted with the eye(s) of the subject suffering from a nucleic acid-related eye disease, such as DED.

a. Nuclease Composition Contact with the Eye(s)

The nuclease composition may be contacted with the eye(s) by any means. The mode of contact with the eye may be such that the nuclease composition is applied topically or injected into the eye. As described herein, when administered topically or injected, the compositions can be formulated in a variety of forms well-known to one of skill in the art. See, e.g., Remington's Pharmaceutical Sciences and Introduction to Pharmaceutical Dosage Forms, 19th ed., Mack Pub. Co., Easton, Pa. (1995). The nuclease composition may be formulated pharmaceutically acceptable carrier as described herein. See Section 3(b), for example.

Dosages, effective amounts, and other routes of administration to bring the DNase composition into contact with the eye(s) are also described above under the section entitled "Pharmaceutically Acceptable Carrier."

b. Nucleic Acid-Related Eye Disease

The nucleic acid-related eye disease may be caused by autoimmune conditions, decreased tear production, microbial infection, a change in tear composition, and/or environmental conditions. Such conditions may decrease the rate of blinking and/or result in inadequate lubrication of the eye, for example. The subject may be identified as suffering from a nucleic acid-related eye disease or a related disorder by detecting a sign or symptom selected from the group consisting of dry, scratchy, stingy, itchy, burning or pressured sensations, irritation, pain, redness, inflammation, discharge, and excessive eye watering. The subject's tear composition may be insufficient for proper eye tissue lubrication. The nucleic acid-related eye disease may provide an environment on, in, or around the eye for inflammation, bacterial proliferation and/or bacterial infection. The nucleic acid-related eye disease may be caused by tear film, such as biofilm or mucoid film, on or in the eye. Tear film may form on materials that come in contact with the eye, such as contact lenses, or materials implanted in the eye, such as scleral buckles, intraocular lenses, keratoprostheses and glaucoma drain implants.

The nucleic acid-related eye disease may be the result of the dysregulation of nucleic acid production and clearance mechanisms, whereby tear fluid and film nuclease level and/or activity are deficient, which allows extracellular DNA, for example, and neutrophil extracellular traps (NETS) to accumulate in tear film and drive ocular surface inflammation. The nucleic acid-related disease may be caused by a decrease in nuclease activity, or a decrease in the level of nuclease, in the tears as compared to normal subjects.

The nucleic acid-related eye disease may be dry eye disease, ocular cicatricial pemphigoid (OCP), keratoconjunctivitis sicca (KCS), Sjogren syndrome (SS), Sjogren syndrome associated keratoconjunctivitis sicca, non-Sjogren syndrome associated keratoconjunctivitis sicca, keratitis sicca, sicca syndrome, xerophthalmia, tear film disorder, decreased tear production, aqueous tear deficiency (ATD), meibomian gland dysfunction (MGD), and evaporative loss, diffuse lamellar keratitis, contact lens-associated keratitis, endophthalmitis, or infectious crystalline keratopathy. The nucleic acid-related eye disease may be an allergic eye condition. The allergic eye condition may result from the presence of NETS or eosinophil extracellular traps.

The level of nuclease in the tears or tear film of a subject having a nucleic acid-related disease may be less than 3.14 ng/ml of nuclease. For example, the level of nuclease in the tears of a subject having a nucleic acid-related disease may be less than 3.00 ng/ml of nuclease; less than 2.50 ng/ml of nuclease; less than 2.00 ng/ml of nuclease; less than 1.50 ng/ml of nuclease; less than 1.00 ng/ml of nuclease; less than 3.00 ng/ml of nuclease; less than 0.50 ng/ml of nuclease; or less than 0.25 ng/ml of nuclease. The level of nuclease activity in the tears or tear film of a subject having a nucleic acid-related disease may be equal to, or less than, 0.05 Kunitz units. The level of nuclease activity in the tears of a subject having a nucleic acid-related disease may be less than 0.04 Kunitz units; less than 0.03 Kunitz units; less than 0.02 Kunitz units; less than 0.01 Kunitz units; or less than 0.05 Kunitz units. One Kunitz unit may be defined as the amount of nuclease enzyme that causes an increase in absorbance at 260 nm of 0.001 per mL when acting upon highly polymerized DNA at 25° C. and pH 5.0 under specified conditions.

(1) Tear Film

The tear film, which may contain an accumulation of nucleic acid and NETs, may be a biofilm or a mucoid film. The biofilm may be produced by bacteria. The mucoid film may be produced by the conjunctiva of the eye. The mucoid film or biofilm may be present in allergic eye conditions. The biofilm and mucoid film on the ocular surface, or inside the eye, of a subject having a nucleic-acid-related eye disease may contain extracellular DNA, NETS, and/or neutrophils. The NETS may contain extracellular DNA, histones, cathelicidin, and/or neutrophil elastase.

(a) Dry Eye Disease (DED)

The DED may be any disease or disorder of the eye that can be attributed to any one of a number of factors. In some variations, the DED to be treated is DED caused by any condition other than an alloimmune response. Alloimmune responses may result, for example, in some corneal transplant patients. More specifically, in some variations, the DED to be treated is an autoimmune DED or a DED associated with Sjogren's syndrome. The DED may be due to the presence of extracellular DNA on the ocular surface, excessively fast tear evaporation (evaporative dry eyes) and/or inadequate tear production. Also see FIG. 1 and description thereof. In some variations, the dry eye disease is attributable to one or more causes selected from: aging, contact lens usage and medication usage. In some variations, the dry eye disease is a complication of LASIK refractive surgery. In other variations, the DED arises in a subject who has not had eye surgery of any kind, e.g., treatment of subjects in whom the DED is not caused by LASIK surgery, corneal transplant surgery, or other ocular surgeries.

Extracellular DNA, NETs, and neutrophils may be present on the ocular surface of a DED subject and abundant in mucoid film and/or biofilm. The NETs may consist of extracellular DNA, histones, cathelicidin, and neutrophil elastase. Tear fluid nuclease activity may be significantly decreased in the DED subject, whereas the amount of extracellular DNA on the ocular surface may be increased. Expression of genes downstream of extracellular DNA signaling, such as TLR9, MyD88, and type I interferon, as well as the inflammatory cytokines interleukin-6 and tumor necrosis factor α may also be increased in DED patients. The nuclease activity deficiency may allow for extracellular DNA and NETs to accumulate in tear film, such as precorneal tear film, mucoid tear film, or biofilm, and may result in ocular surface inflammation.

4. Method of Treating an Ocular Infection

Extracellular nucleic acid is a component of tear film. The nuclease composition described herein may be used to treat bacterial infections and inflammation related to biofilm formation, either on the ocular surface or inside the eye (intraocular).

Provided herein is a method of treating an ocular infection and/or ocular-inflammation. The nuclease composition may be contacted with the eye(s) of the subject suffering from the infection. The infection may be a bacterial infection or a viral infection. The composition may be brought into contact with the eye as described above (see Section 3(a)), such as by topical application to the ocular surface or by injection into eye. Accordingly, the composition may be used intraocularly.

5. Kit

Provided herein is a kit, which may be used for treating or diagnosing a nucleic acid-related eye disease. The kit may comprise a nuclease. The nuclease may be a nuclease composition comprising an ophthalmic excipient. The composition may contain one or more of an antibiotic compound(s), antiviral compound(s), a toll-like receptor antagonist(s), a type-1 interferon antagonist(s), a cathelicidin inhibitor(s), and/or a neutrophil elastase inhibitor(s) in a container, for use in treatment of the affected eye(s). The kit may comprise a nuclease composition and one or more of an antibiotic compound(s), a toll-like receptor antagonist(s), a type-1 interferon antagonist(s), a cathelicidin inhibitor(s), and/or a neutrophil elastase inhibitor(s) in two or more containers, for use in treatment of the affected eye(s). The kit may comprise a pipette or filter paper as sample collection means. The pipette or filter paper may be used to collect tears from the eye surface. The two or more containers may be packaged together, for example, in a cardboard box. The kit may also include a set of usage instructions, which refer to the nuclease composition and, if present, the antibiotic compound(s), the antiviral compound(s), a toll-like receptor antagonist(s), a type-1 interferon antagonist(s), a cathelicidin inhibitor(s), and/or a neutrophil elastase inhibitor(s). The instructions may describe how to perform and/or monitor the method described herein.

6. Method of Diagnosis

Provided herein is a method for determining whether a subject has a nucleic acid-related eye disease. The method may comprise collecting a tear sample from a subject. The sample may be obtained by using the kit described above. This sample may be contacted with a dye that binds to nucleic acid, such as picogreen. Alternatively, the sample may be contacted with a nucleic acid and then contacted with the dye. The intensity of the color may be measured and compared to the intensity of dye fluorescence in a normal control sample. An increased level of dye fluorescence intensity in the sample as compared to the control may be indicative of a dry eye disease. The dye intensity may be indicative of the level of extracellular nucleic acid on surface of the eye. The dye intensity and, therefore, the level of extracellular nucleic acid, may be indicative of the severity of the disease. For example, if picogreen is used, a high green color intensity, especially compared to a control (i.e. a negative control), may indicate that the subject has severe dry eye disease. Depending on the type of dye used, the level of nuclease on the eye surface may also be determined using this method.

The present invention has multiple aspects, illustrated by the following non-limiting examples.

EXAMPLES

Example 1

Methods for Determination of Extracellular DNA on Ocular Surface (Also See FIGS. 2-9 and Descriptions Thereof)

Samples were collected from dry eye patients using Schirmer's test paper. Schirmer's test is a routine test conducted during ocular examination. Schimer Test consists of a thin strip of filter paper placed under lower lateral eyelid for 5 minutes. The strip of paper is then taken out and measured for amount of wetting of the paper. It is measured in millimeters. If the value is less than 5, it is diagnostic for dry eye disease. Usually after the test this strip of paper is discarded. However, in the present study, this paper was used instead of discarding it.

As the paper touches the palperbal and bulbar conjunctiva, the cells from these areas adhere to the filter paper. Cells from the paper were collected on silane coated adhesive coated slides from Tekdon Corporation. Four slides were obtained in this process from each patient. The slides were stored in 10% formaldehyde for at least half an hour before staining. These slides were then stained with hematoxylin and eosin, immunostained with neutrophil elastase, histone, and myeloperoxidase antibodies for presence of NETs. The slides were then immunostained with Caspase 3 antibody for apoptosis.

With respect to hematoxylin and eosin staining, the cells were fixed in 10% formaldehyde for at least half an hour. The slide was dipped in hematoxylin for 7 mins followed by wash. Then the slide was dipped 4 times in acid rinse followed by wash and then dipped in bluing agent for 2 mins. The slide is briefly washed followed by eosin dip for 2 mins. After washing the slide is air dried at room temperature, covered by coverslip and visualized under light microscope.

Double immunostaining was performed using antibodies for (a) neutrophil elastase (Dakocytomation-Monoclonal Mouse anti-human neutrophil elastase) and histones (Santa Cruz Biotechnology, Santa Cruz, Calif.) along with 4',6-diamidino-2-phenylindol i.e. DAPI (Vector Labs, Burlingame, Calif.), (b) Myloperoxidase and histones (Santa Cruz Biotechnology, Santa Cruz, Calif.) along with DAPI to show the presence of NETs on the ocular surface. The cells on the saline coated slides were fixed in 10% formaldehyde at least for half an hour. Then slides were washed two times, using PBS+0.025% Triton-X 100, 5 minutes with shake. Then the cells were blocked with 10% normal serum+1% BSA in PBS for 2 hours at room temperature. The primary antibody was diluted using PBS in the ratios of 1:400 for neutrophil elastase and 1:200 for histones. And the slides with primary antibody were incubated overnight at 4° C. After overnight incubation, the cells were washed two times using PBS+0.025% Triton, 5 minutes with shake. In the next step, the secondary antibody for neutrophil elastase (red) and (green) for histones were added, which was diluted using PBS+1% BSA, and incubated at room temperature for 1 hour. After 1 hour slides were rinsed in PBS three times for 5 minutes and counterstained with DAPI (Vector Labs, Burlingame, Calif.). Later the slides were visualized under inverted microscope (Carl Zeiss Meditec GmbH, Hamburg, Germany).

For quantification of the extracellular DNA, filter papers containing the extracellular DNA and the cells were incubated with 100 U/mL DNase1 (from Fermentas Life Sciences, Hanover, Md.). 0.5 M EDTA was then added to stop nuclease activity and collected the supernatants. Picogreen (Invitrogen, Carlsbad, Calif.), a DNA fluorescent DNA dye, was added, and the DNA content was quantified by fluorescence spectrometry.

DNase treatment: Four samples from conjunctiva were collected for each patient and treated with: Sample 1—Stained with DAPI (control); Sample 2—Treated with DNase (100 IU/ml for 20 minutes) and stained with DAPI; Sample 3—Treated with heat inactivated DNase (100 IU/ml for 20 minutes) and stained with DAPI; Sample 4—Soaked in PBS and stained with DAPI.

Samples were then visualized under inverted microscope (Carl Zeiss Meditec GmbH, Hamburg, Germany). Quantification was performed by taking images using Axiovision and Neurolucida software. The values were calculated and the graphs were plotted using Microsoft Excel. See FIG. 9 and description thereof.

Example 2

Method Used in Examples 3 and 4

Study Population: Symptomatic tear-deficient DED patients and asymptomatic healthy individuals with normal tear production were enrolled and provided written informed consent according to the Helsinki statement under an Institutional Review Board approved protocol. Patients were included if they complained of any DED symptom (dryness, irritation, grittiness, light sensitivity, or foreign body sensation) and additionally had severe aqueous tear deficiency, defined as Schirmer I value ≤5 mm in 5 minutes (without anesthesia). Individuals were included in the control group if they had no ocular symptoms and a Schirmer I value ≥12 mm in 5 minutes (without anesthesia).

Conjunctival Exfoliated Cells and Mucoid Films Analyses: The Schirmer I test was performed without topical anesthesia by placing Schirmer test strips (Haag-Streit, Essex, UK) over the lower lid margin, at the lateral and middle third junction, for 5 minutes. Strip wetting was recorded in millimeters. Because the test strips contact the palpebral and bulbar conjunctiva, cells from these areas are exfoliated upon strip removal. Cells that adhere to the strips were transferred to silane-coated adhesive slides. Slides were immediately fixed for 30 minutes in neutral buffered 10% formaldehyde (Sigma-Aldrich, St. Louis, Mo.) before further analyses. Mucoid films were collected using disposable microcapillary glass tubes (5 µl volume; Sigma-Aldrich) over the bulbar conjunctiva or from inferior conjunctival fornix. The mucoid films were spread on silane-coated slides and processed.

Hematoxylin and Eosin (H&E) staining: Slides with conjunctival exfoliated cells (n=15) or mucoid films (n=10) were stained with hematoxylin (H-3401, Vector Labs, Burlingame, Calif.), rinsed in acid, dipped in bluing solution, and counterstained with eosin (Thermo Scientific, Waltham, Mass.). Slides were examined using an upright Axioscope 100 microscope (Carl Zeiss Meditec GmbH, Hamburg, Germany), imaged using a Zeiss MRc color camera, and analyzed using Zeiss Axiovision.

Immunostaining and Confocal Microscopy: Immunofluorescence staining and confocal microscopy were performed to localize molecular components of NETs and extracellular DNA (eDNA) as previously described. Slides were permeabilized for 5 minutes in 0.025% Triton X-100 and blocked for 2 hours at room temperature with 1% bovine serum albumin (BSA) and 10% normal donkey serum in PBS. Slides were incubated overnight at 4° C. with the primary antibody diluted in blocking solution (1:200). The slides were washed four times in PBS (15 min each) and incubated for 1 hour with the secondary antibody diluted in blocking solution (1:200). Vectashield mounting medium with 4',6-diamidino-2-phenylindole (DAPI; Cat. #H-1200, Vector Labs) was placed over the slides and covered with a glass coverslip. The primary antibodies used were: (1) mouse monoclonal anti-human neutrophil elastase (clone NP57, DAKO, Glostrup, Denmark); (2) goat polyclonal anti-histone H2B (Cat. #SC-8650, Santa Cruz Biotechnology, Santa Cruz, Calif.); and (3) rabbit polyclonal anti-cathelicidin (Cat. #ab64892, Abcam, Cambridge, Mass.). The secondary antibodies used were Dylight 594-conjugated anti-mouse IgG for neutrophil elastase, (1:1000, Jackson Immunoresearch Laboratories, West Grove, Pa.) and FITC 480 anti-goat IgG for histone and cathelicidin (1:200, Jackson Immunoresearch Laboratories). Specimens were analyzed using a LSM 710 META confocal microscope (Carl Zeiss Meditec GmbH, Hamburg, Germany). Patient samples were imaged first to optimize the fluorescent signals, and immediately thereafter, negative control slides (with the primary antibody omitted) were imaged using the identical settings. The specificity of the primary antibodies anti-neutrophil elastase and anti-cathelicidin has been previously validated.

Lacrimal gland DNase I immunostaining: Lacrimal gland sections (6-8 µm) were obtained from archived non-inflammatory and non-malignant lacrimal biopsies (n=5). Sections were deparaffinized at 56° C. for 30 minutes, followed by a graded alcohol series treatment. Sections were processed for staining as described above. The primary antibody used was rabbit polyclonal anti-DNase I (1:50, Cat. #HPA010703, Sigma Prestige, St. Louis, Mo.). The secondary antibody was Dylight 594-conjugated anti-rabbit IgG. Negative controls were: (1) primary antibody omitted, (2) rabbit polyclonal IgG isotype control (Cat. #ab27427, Abcam), and (3) peptide pre-incubation with primary antibody (Peptide for Cat #HPA010703, Atlas Antibodies AB, Stockholm, Sweden). Imaging and analyses were performed as described above.

Laser Capture Microdissection of eDNA strands: Schirmer test strip impressions were taken on membrane slides (Cat #11505158, Leica, Solms, Germany) as described above. Slides were fixed in 10% formaldehyde for 30 minutes and washed in 1×PBS. The slides were stained with DAPI, briefly washed in PBS, and dried for 30 minutes at 37° C. DAPI-stained eDNA strands were visualized, dissected, and captured using PALM laser capture microdissection microscope (Carl Zeiss, Thornwood, N.Y.). Captured strands were collected in an adhesive cap, and DNA was extracted using DNAzol (Cat. #1-0503-027, Invitrogen, Carlsbad, Calif.) according to the manufacturer's protocol. PCR was performed using the GoTaq PCR kit (Cat. #M7122, Promega, Madison, Wis.) per the manufacturer's protocol. The human GAPDH gene (Cat. #PPH00150F, SA Biosciences, Frederick, Md.) was amplified using gene specific primers. PCR products were electrophoresed and visualized on a 2% ethidium bromide-stained agarose gel.

Quantification of ocular surface eDNA: We used two strategies to calculate the amount of eDNA on the ocular surface. First, the total length of eDNA strands was determined in exfoliated material derived from the Schirmer test strip impressions on glass slides. Second, eDNA was extracted from the Schirmer test strip using DNase I and determined the fluorescence intensity using picogreen DNA fluorescent dye.

eDNA length: Slides with Schirmer strip impressions were fixed and stained with DAPI. Five random 20× objective fields were imaged using an inverted microscope (Axio Observer, Zeiss) and analyzed using Neurolucida software (MBF Bioscience, Williston, Vt.). The eDNA fibers were traced and lengths were calculated using Neuroexplorer (MBF Bioscience) as previously described for corneal nerves. The average total eDNA length in dry eye patients (n=10) was compared to that in normal controls (n=10).

Picogreen assays: Picogreen assays were performed as previously described. The folded end of the Schirmer strip that contacted the conjunctiva was collected in an eppendorf tube and 200 µl of 100 U/ml DNase I (Cat. #EN0521, Fermentas Life Sciences, Hanover, Md.) was added. After 20 minutes, nuclease activity was stopped with 0.5 mM of EDTA and the Schirmer strip end was removed. Picogreen DNA fluorescent dye (Cat. #P7589, Invitrogen Detection Technologies) was added, and fluorescence intensity was determined using a microplate reader (Synergy H1, BioTek, Winooski, Vt.). Values were averaged and compared between DED patients (n=10) and normal controls (n=10).

Exfoliated Conjunctival Cell Gene Expression: RNA was extracted from exfoliated conjunctival cells on Schirmer test strips from DED patients (n=20) and normal controls (n=16). The folded ends of Schirmer test strips were placed directly in TRIzol (Invitrogen) for RNA extraction, which was performed according to the manufacturer's protocol. Reverse transcription was performed with 1000 ng total RNA using the $RT^2$ First Strand cDNA Synthesis Kit (SABiosciences). The resulting cDNA was pre-amplified using $RT^2$ Nano PreAMP Kit according to the manufacturer's instructions. Real-time quantitative PCR (qPCR) was performed with SYBR using a 7900HT ABI real-time instrument. cDNA signaling gene expression and inflammatory cytokines were analyzed by real-time qPCR.

All primers and reagents were purchased from SABiosciences unless specified otherwise. The primers used were toll-like receptor 9 (TLR 9; Cat. #PPH01809A), interferon-a (INFA; Cat. #PPH01321A), MyD88 (Cat. #PPH00911A), interferon-β (INFB; Cat. #PPH00384E), IL-6 (Cat. #PPH00560B), TNF-α (Cat. #PPH00341E), and glyceraldehyde-3-phosphate dehydrogenase (GAPDH; Cat. #PPH00150F). Samples were assayed in duplicate in a total volume of 25 µl using the following cycling conditions: 10 minutes at 95° C., 40 cycles of 95° C. for 15 seconds, and 60° C. for 60 seconds. A human genomic DNA contamination control was used to confirm that amplification reagents were not contaminated with genomic DNA. For data analyses, the cycle threshold (CT) of each gene for DED patients was normalized to the corresponding value for normal subjects and used to calculate fold change using $2^{-\Delta\Delta^{CT}}$ method.

Nuclease activity and DNase I in tear fluid: Tears were collected using disposable microcapillary glass tubes using slit lamp biomicroscope. The tubes were placed in the lower conjunctival fornix, and tears were collected by capillary action. Tears were transferred to DNase-free eppendorf tubes for analyses.

Nuclease activity in normal tear fluid: Tear film nuclease activity was quantitated in DED patients (n=5) and normal controls (n=5) using a DNA digestion assay (DNase detection kit, MO-BIO Laboratories, Carlsbad, Calif.) per the manufacturer's instructions. Tear samples and DNA standards (1-kb DNA ladder) were electrophoresed on a 2% ethidium bromide-stained agarose gel and photographed using a UV-transilluminator. DNase activity is evaluated by comparing the band intensity and pattern of the DNA standard with that of the tear samples. If nucleases are present in tear fluid, there is smearing and decreased band intensity in the sample lanes. If the DNA ladder is completely degraded, the nuclease activity is greater than 0.05 Kunitz units, which is the upper limit of detection with this method.

Nuclease activity in tear fluid: A fluorescence resonance energy transfer (FRET)-based assay was used to compare total nuclease activity in tear fluid from DED patients (n=17) and normal controls (n=15). FRET nuclease assays were performed. The FRET substrate, a PRIMETIME™ qPCR probe was purchased from Integrated DNA Technologies (Coralville, Iowa). It consists of a short (15mer) single-stranded oligonucleotide that is modified at the 5' end with a Cy3 fluorophore and at the 3' end with Black Hole Quencher 2 (BHQ2). The sequence of the oligonucleotide substrate is 5' CCC CGG ATC CAC CCC 3' (SEQ ID NO:2). When the oligonucleotide is intact, the Cy3 and BHQ2 are close enough to quench fluorescence. Upon oligonucleotide cleavage, Cy3 fluorescence is proportional to the amount of cleavage and can be used to quantify nuclease activity. Considerable variation in yield of HPLC purified FRET substrate was observed in the three orders (21.1 and 35.8 nmoles for the 250 nmoles synthesis order and 124.5 nmoles for the 1 μmole synthesis order), therefore we have not pooled the data and have reported tear fluid nuclease activity analysis performed with 1 μmole order. The variation in yield comes from the HPLC purification process and is inversely related to the FRET substrate purity. Tear samples were collected as described above. The samples were incubated on ice until the assay was performed. The assay was performed within 3 hours of sample collection. Tear samples (5 μl) were added to a microtiter plate. FRET substrate (2.5 nmol in 50 μl buffer solution) was added to wells containing the tear samples. The fluorescence emitted (RFU) and the rate of fluorescence change were measured using the microplate reader (Synergy H1, BioTek) at 37° C., excitation 552 nm, and emission 580 nm. Plates were agitated for 5 seconds before the readings and readings were taken at 3-second intervals for 30 minutes. For analyses, the kinetic RFU measurements for each patient were averaged over 30 minutes.

DNase I quantification in tear fluid: We used a commercially available human DNase 1 ELISA Kit (Cat. #E0100214, Life Sciences Advanced Tech, St. Petersburg, Fla.) to determine the amount of DNase I in tear fluid. Twenty-five microliters of tear fluid (n=5) and 0.5 ml of saliva (n=5) were collected from healthy subjects. Saliva was centrifuged at 15,000 rpm for 5 min at 4° C., and 25 μl of the supernatant was analyzed. The standard or samples (25 μl) were added to the appropriate well in the antibody pre-coated microtiter plate, and the assay was performed per the manufacturer's instructions. The sensitivity of this assay is 0.1 ng/ml.

Statistical Analyses: Mean values and standard errors of the mean were computed for DED patients and normal subjects and analyzed using Student t-tests. Microsoft Excel office statistics software packages were used for analyses and graphs. p≤0.05 was considered statistically significant.

Figure 11:
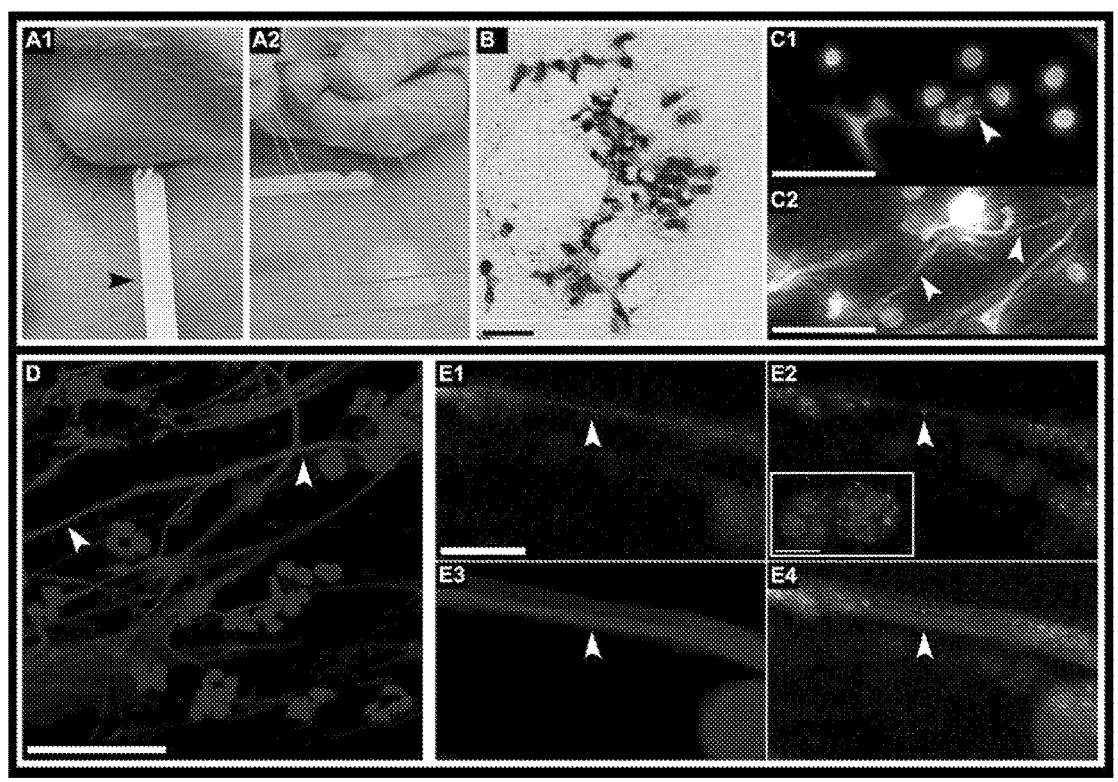
FIG. 11 shows material derived from Schirmer test strip impressions. (A1, A2): Impression cytology method using Schirmer test strips (A1, arrowhead) and silane coated glass slides (A2). (B): H&E staining showing exfoliated surface cells. (C): Wide-field fluorescent microscope image after DAPI stain of conjunctival impression material reveals short and sparse extracellular DNA (eDNA) strands (arrowhead) in normal subjects (C1) and numerous long eDNA strands (C2) in DED patients (arrowhead). (D): Confocal immunofluorescence image after DAPI staining demonstrates numerous strands (arrowhead) and neutrophils with multilobed nucleus. (E): Confocal immunofluorescence staining image shows that histones (E1, green), neutrophil elastase (E2, red), and eDNA (E3, Blue) are the molecular components of NETs (E4, overlay). Arrowhead indicates a NET strand. Inset in E2 shows neutrophils with DAPI-stained multilobed nucleus. Scale bars: B, C1, C2, and D (50 μm); E1 and E2 inset (10 μm).

Example 3 eDNA and Neutrophil Extracellular Traps (NETs) are Present on the Ocular Surface The study population included DED patients (n=37 patients, 73 eyes), who had an average aqueous tear production of 2.76±0.35 mm. Normal individuals (n=18 individuals, 36 eyes) had an average aqueous tear production of 19.1±1.25 mm, which was significantly greater than DED patients (p<0.001). Patients had non-Sjogren dry eyes (n=33), which included etiologies such as idiopathic, post-LASIK, neurotrophic and ocular cicatricial pemphigoid, and Sjogren disease (n=4).

eDNA and Neutrophil extracellular traps (NETs) are present on the ocular surface: H&E and immunofluorescence staining was performed on conjunctival cells from patients with severe DED. Cells were derived from test strip impressions on a glass slide after performing Schirmer I test (FIG. 11, A1, A2). H&E staining showed exfoliated conjunctival cells present singly or in groups. The cells were round or oval shaped, with an eosiniophilic cytoplasm and uniform round basophilic nuclei (FIG. 11, B). DAPI nuclear staining revealed a few sparse eDNA strands in normal subjects (FIG. 11, C1) and numerous long eDNA stands in DED patients (FIG. 11, C2). Confocal microscopy revealed neutrophils were present among the eDNA strands (FIG. 11, D). Histone (FIG. 11, E1) and neutrophil elastase (FIG. 11, E2) colocalized with DAPI stained eDNA strands, confirming that these were NETs (FIG. 11, E4). To rule out the possibility that eDNA could be an artifact of impression cytology, analyses were performed on exfoliated buccal mucosa cells obtained using identical methodology. eDNA strands were not observed (data not shown).

Figure 12:
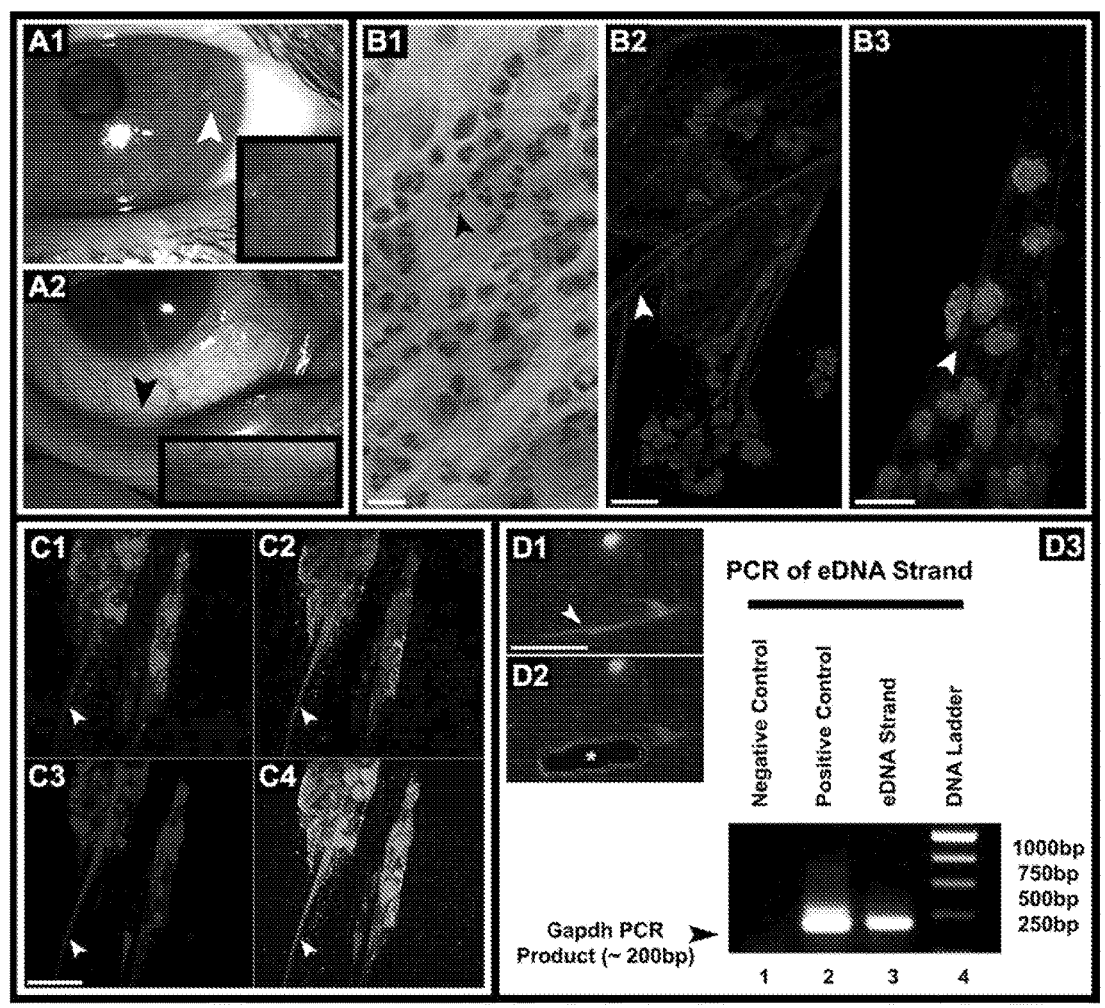
FIG. 12 shows eDNA and neutrophil extracellular traps (NETs) in mucoid films. (A): Clinical photographs of eyes of patients with severe tear deficient DED. Arrowhead indicates a mucoid film over the cornea and bulbar conjunctiva (A1), and inferior fornix (A2). Inset shows magnified view of mucoid films. (B): cytological examination of the mucoid films. (B1): H&E staining shows the surface epithelial cells and numerous neutrophils. (B2): DAPI staining shows the presence of eDNA strands (arrowhead) and multilobed nucleus of neutrophils. (B3): Neutrophil elastase immunostaining (red) confirms the presence of neutrophils. (C): Confocal immunofluorescent staining image shows that neutrophil elastase (C1, red), histones (C2, green), and eDNA (C3, Blue) are molecular components of NETs (C4, overlay). Arrowhead indicates a NET strand. (D): Laser capture microdissection (LCM) was performed to capture DAPI-stained strands to confirm the presence of DNA in them. In D1, arrowhead indicates an eDNA strand. In D2, asterisk occupies the area of the strand post LCM. (03): GAPDH PCR product in eDNA strand lane confirms the presence of DNA material. Scale bars: B1, B2, and B3 (20 µm); C, D1, and D2 (50 µm).

H&E and immunofluorescence staining were performed on mucoid films present on the bulbar conjunctiva/cornea (FIG. 12, A1) or in the inferior fornix (FIG. 12, A2). Mucoid films appeared as a frothy white mucoid collection that sometimes dispersed with blinking. A microcapillary tube was used to lift these mucoid films for analyses. In some instances, turbid white fluid was drawn in the microcapillary tube. However, the analyses still revealed similar findings. H&E showed numerous neutrophils and exfoliated cells within the mucoid films (FIG. 12, B1). DAPI staining showed eDNA (FIG. 12, B2) and numerous neutrophil elastase positive neutrophils (FIG. 12, B3). Neutrophil elastase (FIG. 12, C1) and histone (FIG. 12, C2) colocalized with DAPI-stained eDNA strands, confirming that these were NETs (FIG. 12, C4).

To confirm that the DAPI-stained strands contained DNA, DAPI-stained strands from membrane slides were captured using a laser capture microdissection microscope (FIG. 12, D1 and D2). The extracellular DAPI-stained strands contain DNA as shown by GAPDH gene product PCR amplification (FIG. 12, D3).

Figure 13:
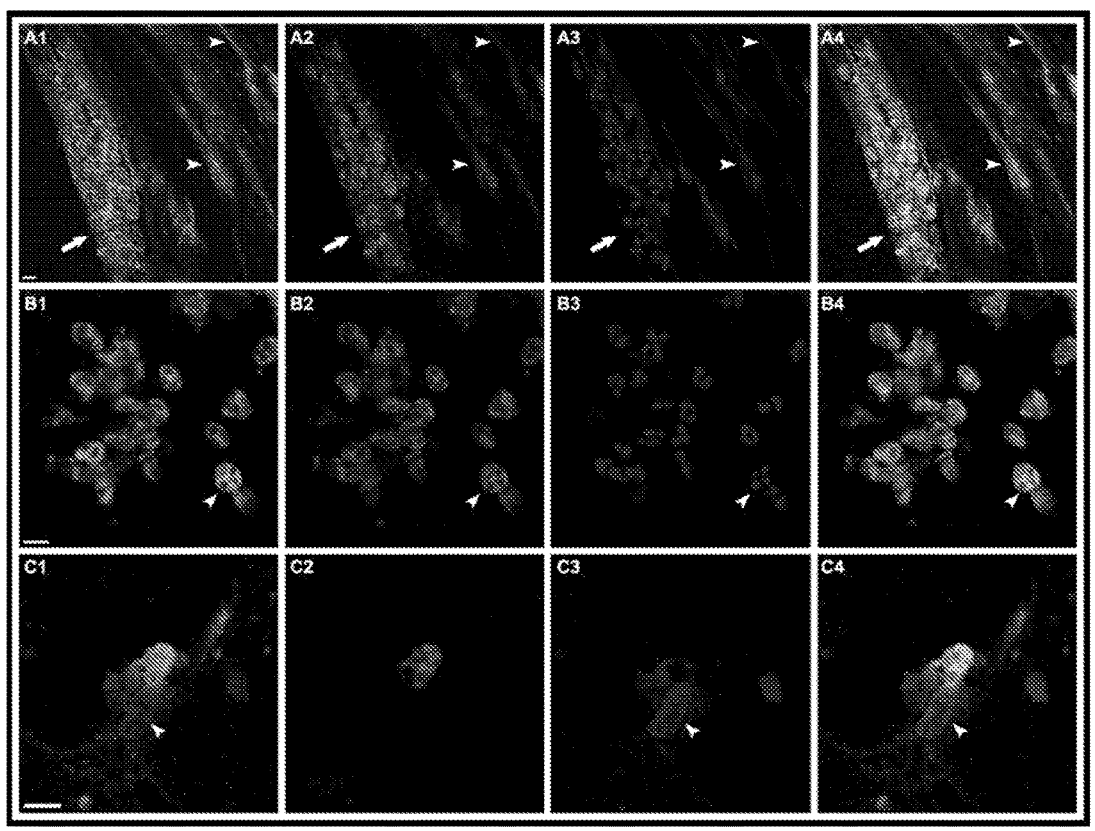
FIG. 13 shows neutrophils (A1-A4): Cathelicidin (green) is present in mucoid films (A1, arrow) and eDNA strands (A1, arrowhead). Cathelicidin colocalizes with neutrophil elastase (A2, red) and DAPI nuclear stain (A3, blue). (B1-B4): Cathelicidin (green) is present in neutrophils (B1, arrowhead) and colocalizes with neutrophil elastase (B2, red) and DAPI (B3, blue). (C1-C4): Cathelicidin (C1, arrowhead) and DAPI-stained nuclear material (C3, arrowhead) are extruded from a neutrophil to form NETs. Scale bars: 10 µm.

The presence of cathelicidin in NETs was investigated: cathelicidin was present within mucoid films (FIG. 13, A1) and colocalized with neutrophil elastase and DAPI-stained nuclear material (FIG. 13, A4). Cathelicidin was also present within neutrophils (FIG. 13, B4). Cathelicidin, nuclear material, and neutrophil elastase extrude from the neutrophil to form NETs (FIG. 13, C1-4).

Figure 14:
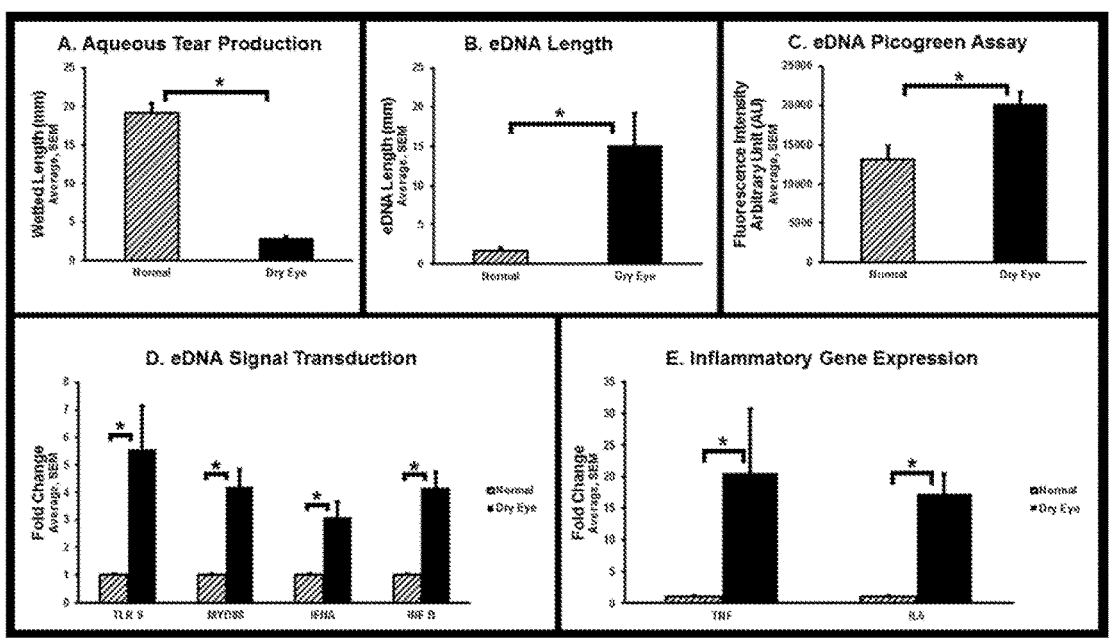
FIG. 14 shows gene expression in DED patients and controls. (A): The average aqueous tear production, measured using Schirmer I test, was significantly lower in DED patients. (B): eDNA length was measured after impression of Schirmer strip on a glass slide. The eDNA length was significantly greater in DED patients. (C): eDNA amount on the Schirmer strips was measured using Picogreen assay. DED patients have significantly greater eDNA amounts. (D): Genes in the eDNA signal transduction pathway were significantly overexpressed in exfoliated conjunctival cells from DED patients. (E): Inflammatory gene expression was also significantly increased in DED patients.*p<0.05.

With respect to the amount of eDNA on the ocular surface, DED patients had significantly lower aqueous tear production compared to normal subjects (FIG. 14, A). eDNA strand length was significantly greater (p=0.002) in DED patients (15.0±4.2 mm) compared with normal subjects (1.58±0.47 mm) (FIG. 14, B). The amount of eDNA on the ocular surface, as measured by picogreen assay, was also significantly greater (p=0.006) in DED patients (20137.2±1507.3 RFU) compared to controls (13055.5±1787.2 RFU) (FIG. 14, B).

Example 4 eDNA Signaling Pathway Gene Expression qPCR on exfoliated conjunctival cells was performed to determine the fold change in the expression of genes downstream of eDNA signaling (FIG. 14, D). The expression of TLR9, Myd88, and IFN-type I (IFNA and IFNB), as well as the inflammatory genes IL-6 and TNF-α, was significantly increased in conjunctival cells from DED patients. The fold increase in gene expression in DED patients observed was: TLR9 (5.57±1.6, p=0.003), Myd88 (4.20±0.6, p<0.0001), IFNA (3.09±0.5, p=0.0003), INFB (4.18±0.6, p<0.0001), TNF-a (20.6±10.0, p=0.03), and IL-6 (17.3±3.1, p<0.0001).

Example 5

Nuclease Deficiency in DED Patients

Figure 15:
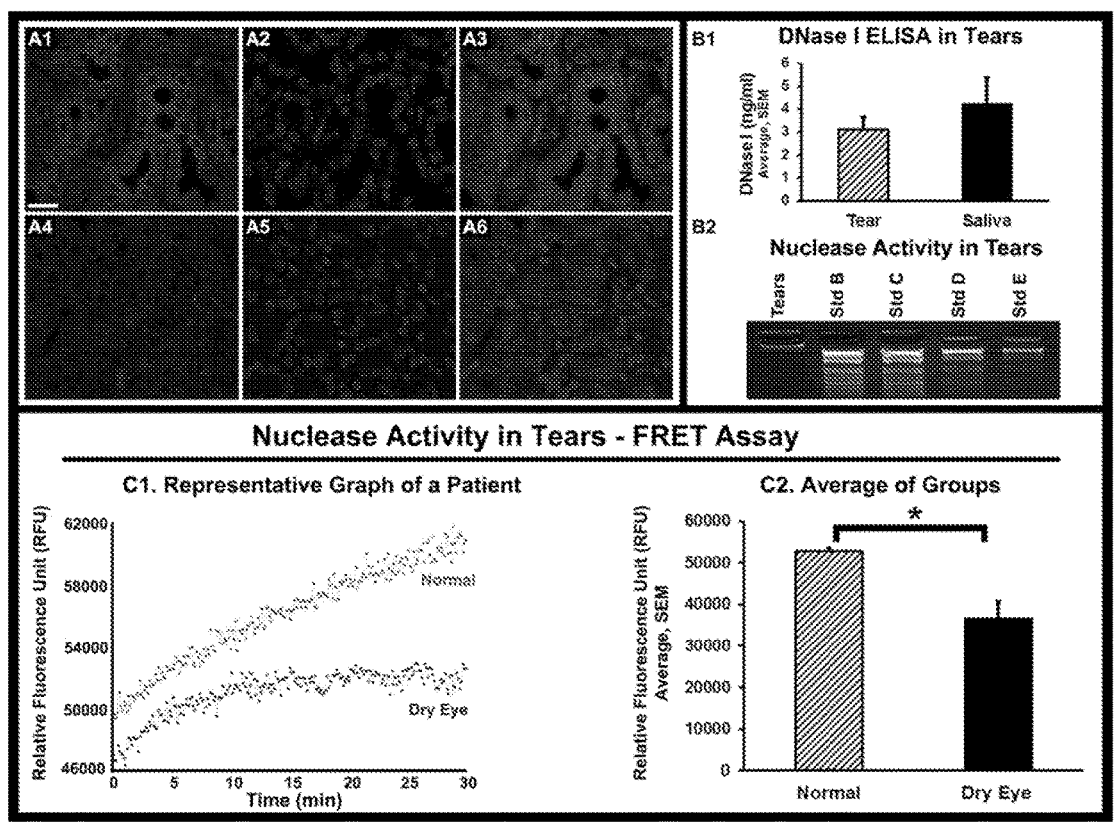
FIG. 15 shows Nucleases and DNase I are present in tear fluid (A1-A6): Immunofluorescent microscope image showing DNase1 in human lacrimal glands (A1-A3, red). The specificity of the staining was confirmed with peptide competition (A4-A6) and isotype control staining (not shown). (B): Nuclease activity in the tears of normal subjects. DNase I ELISA showed that its concentration in normal tear fluid is 3.14 ng/ml. In the DNase Detection Kit, normal tears completely degraded DNA (tears lane). Therefore, tear fluid nuclease activity is greater than 0.05 Kunitz units. (C): Nuclease activity in tears was quantitated using a FRET assay. A representative graph comparing nuclease activity in a DED patient (blue) with a healthy individual (green) shows reduced nuclease activity in the DED patient. (D): The nuclease activity in DED patients was significantly lower compared to healthy individuals. *p<0.05, Scale bars: 20 m.

Nucleases and DNase I are present in tear fluid. DNase I specific antibodies were used to immunostain lacrimal gland sections. DNase I localized within the epithelial cells lining the lacrimal gland acini (FIG. 15, A). ELISA on tear samples was performed to determine the amount of DNase I in tear and saliva (FIG. 15, B1). DNase I concentration in tear was 3.14±0.49 ng/ml and in saliva was 4.21±1.14 ng/ml. Nuclease activity in the tear was quantitated using a DNase detection kit assay (FIG. 15, B2). The nuclease activity in tears of normal subjects and DED patients was greater than 0.05 Kunitz units. This assay could not be used to quantitate and compare tear fluid nuclease activity of DED patients and normal subjects because 0.05 Kunitz units is the upper limit of detection for this method. Therefore, a FRET-based nuclease activity assay was used to compare total nuclease activity between DED patients and normal subjects (FIG. 15, C1). Total nuclease activity was significantly lower in the DED patients (36749.2±3898.6 RFU, p=0.003) compared with controls (52843.6±724.4 RFU) (FIG. 15, C2).

Example 6

Nuclease Mediated Dissolution of NETs

In order to demonstrate the therapeutic value of nuclease treatment on the treatment of eDNA strands associated with DED, exfoliated materials derived from Schirmer strip impressions of DED patients were treated with DNase I. As shown in FIG. 6(A), eDNA strands were abundantly found in untreated exfoliated material that was sampled from the ocular surface of eyes of DED patients. However, after incubation of the same material shown in FIG. 6A with DNase I for 20 minutes, no eDNA strands were discernible (FIG. 6(B)). This result demonstrates that ocular surface eDNA strands can be dissolved by treatment with DNase I.

Example 7

Bacteria in Tear Film

Figure 16:
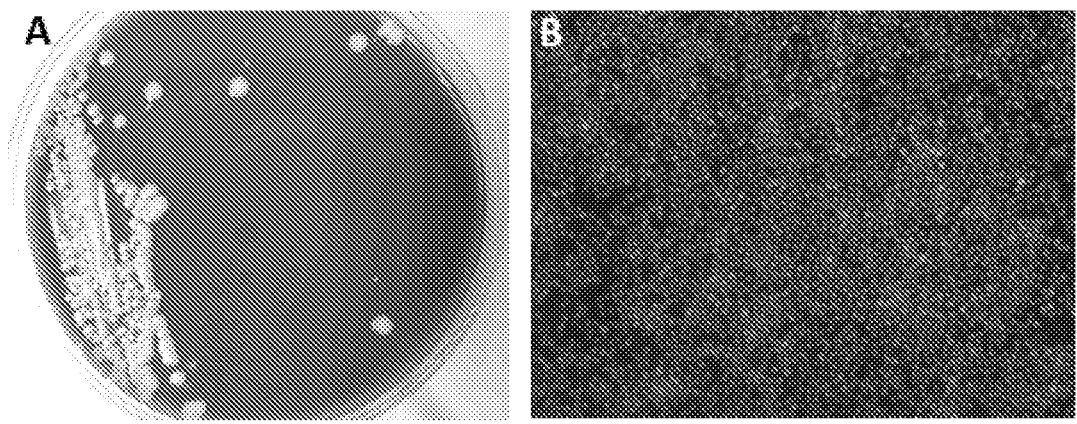
FIG. 16 shows mucoid films plated onto bacterial culture plates. Patients with severe tear deficient dry eye disease may have mucoid films on the ocular surface. Mucoid films were lifted from the ocular surface using a sterile eSwab. Growth of Gram positive cocci was observed which were identified as coagulase negative *staphylococcus* species. (A) Blood Agar culture plate shows pin head bacterial colonies. (B) Baclight live/dead staining of smears from cultured colonies shows live cocci (green) intermixed with dead cocci (red). These experiments confirm that bacteria are present in mucoid films on the ocular surface of the dry eye patients.

Patients with severe tear deficient dry eye disease may have mucoid films on the ocular surface. Mucoid films were lifted from the ocular surface using a sterile eSwab. Growth of Gram positive cocci was observed which were identified as coagulase negative *staphylococcus* species. See FIGS. 16A and B.

I claim:

1. A method for the treatment of an intraocular bacterial infection, comprising administering a composition comprising a nuclease and an ophthalmic excipient to the eye in an amount effective to treat the infection, wherein the composition is injected into the eye.

2. The method of claim 1, wherein the infection is the result of bacterial biofilm formation on or in the eye.

3. The method of claim 1, wherein the nuclease is a DNase, an RNase, or a combination thereof.

4. The method of claim 3, wherein the DNase is an endonuclease or an exonuclease.

5. The method of claim 3, wherein the DNase is selected from the group consisting of Deoxyribonuclease I (DNase I), Deoxyribonuclease II (DNase II), Deoxyribonuclease III (DNase III), micrococcal nuclease, and a recombinant DNase.

6. The method of claim 5, wherein the recombinant DNase I is dornase alpha.

7. The method of claim 3, wherein the RNase is selected from the group consisting of Ribonuclease A (RNase A); Ribonuclease H (RNase H); Ribonuclease I (RNase I); Ribonuclease II (RNase II); Ribonuclease III (RNase III); Ribonuclease D (RNase D); Ribonuclease L (RNase L); Ribonuclease P (RNase P); Ribonuclease PH (RNase PH); Ribonuclease PhyM (RNase PhyM); Ribonuclease R (RNase R); Ribonuclease T (RNase T); Ribonuclease T1 (RNase T1); Ribonuclease T2 (RNase T2); Ribonuclease U2 (RNase U2); Ribonuclease V1 (RNase V1); Ribonuclease V (RNase V); Oligoribonuclease; Exoribonuclease I; Exoribonulcease II; and a recombinant ribonuclease.

8. The method of claim 1, wherein the ophthalmic excipient is selected from the group consisting of a buffer, tonicity adjuster, wetting agent, an antioxidant, and combinations thereof.

9. The method of claim 1, wherein the composition further comprises an antagonist or inhibitor selected from an antibiotic compound, toll-like receptor antagonist, type-1 interferon antagonist, cathelicidin inhibitor, a MyD88 inhibitor, a steroid, an anti-allergy compound, a neutrophil elastase inhibitor, and combinations thereof.

10. The method of claim 1, wherein the composition is in an injectable form.

* * * * *

```
SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 1
ttagggttag ggttagggtt aggg                                          24

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
ccccggatcc acccc                                                    15
```